(12) United States Patent
Sheng et al.

(10) Patent No.: US 10,899,770 B2
(45) Date of Patent: Jan. 26, 2021

(54) CRYSTAL FORM OF ACP-196 SALT AND PREPARATION METHOD, PHARMACEUTICAL COMPOSITION, AND USE THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Tao Zhu, Zhejiang (CN)

(73) Assignee: Hangzhou SoliPharma Co., Ltd., Hangzhou (CN)

( * ) Notice: Subject to any disclaimer, the term of this patent is extended or adjusted under 35 U.S.C. 154(b) by 0 days.

(21) Appl. No.: 16/487,324

(22) PCT Filed: Feb. 20, 2017

(86) PCT No.: PCT/CN2017/074087
§ 371 (c)(1),
(2) Date: Aug. 20, 2019

(87) PCT Pub. No.: WO2018/148961
PCT Pub. Date: Aug. 23, 2018

(65) Prior Publication Data
US 2019/0375755 A1 Dec. 12, 2019

(51) Int. Cl.
| | | |
|---|---|---|
| *A61K 31/4985* | (2006.01) | |
| *C07D 487/04* | (2006.01) | |
| *C01B 17/69* | (2006.01) | |
| *C07C 59/245* | (2006.01) | |

(52) U.S. Cl.
CPC ............ *C07D 487/04* (2013.01); *C01B 17/69* (2013.01); *C07C 59/245* (2013.01); *C07B 2200/13* (2013.01)

(58) Field of Classification Search
CPC .................... A61K 31/4985; C07D 487/04
See application file for complete search history.

(56) References Cited

U.S. PATENT DOCUMENTS

| 9,758,524 B2 | 9/2017 | Barf |
|---|---|---|
| 2017/0044136 A1 | 2/2017 | Cohen |

FOREIGN PATENT DOCUMENTS

| CN | 100352817 C | 12/2007 |
|---|---|---|
| CN | 103889987 A | 6/2014 |
| WO | WO-2017002095 A1 | 1/2017 |
| WO | WO-2018148961 A1 | 8/2018 |

OTHER PUBLICATIONS

International Search Report and Written Opinion for International Application No. PCT/CN2017/074087, State Intellectual Property Office of the P.R. China, dated Nov. 14, 2017, 15 pages.

*Primary Examiner* — Brenda L Coleman
(74) *Attorney, Agent, or Firm* — Sterne, Kessler, Goldstein & Fox P.L.L.C.

(57) ABSTRACT

The present invention relates to novel crystalline forms of ACP-196 (acalabrutinib) salts, compared with the known solid form of ACP-196, the crystalline forms of ACP-196 salts of the present invention have advantages in crystallinity, solubility and hygroscopicity. The present invention also relates to the preparation methods for the preparation of the crystalline forms of ACP-196 salts, pharmaceutical compositions thereof and their uses in the preparation of methods for treating and/or preventing diseases mediated by Bruton tyrosine kinase (BTK), such as autoimmune diseases or disorders, xenoimmune diseases or disorders, cancer, including lymphoma and inflammatory diseases or disorders.

14 Claims, 13 Drawing Sheets

CRYSTAL FORM OF ACP-196 SALT AND PREPARATION METHOD, PHARMACEUTICAL COMPOSITION, AND USE THEREOF

FIELD OF THE INVENTION

The present invention relates to the technical field of crystallization in pharmaceutical chemistry. Specifically, the present invention relates to novel crystalline forms of ACP-196 salts, preparation methods and pharmaceutical compositions and uses thereof.

BACKGROUND

ACP-196 is a second-generation Bruton's tyrosine kinase (BTK) inhibitor that can be used to treat or prevent Bruton's tyrosine kinase-mediated diseases and symptoms such as chronic lymphocytic leukemia (CLL). The drug works by permanently binding to BTK. BTK is part of a chain of protein chains that transmit growth signals from the surface of CLL cells to genes in the nucleus, causing cancer cells to survive and grow. By blocking BTK, ACP-196 can stop the transmission of these growth signals and thus CLL cells die.

ACP-196, has the chemical name of 4-[8-amino-3-[(2S)-(1-(1-oxo-2-butyn-1-yl)-2-pyrrolidinyl]imidazo[1,5-a]pyrazin-1-yl]-N-2-pyridinebenzamide, and its English name is acalabrutinib, with CAS No. 1420477-60-6. The chemical structure of ACP-196 is shown in the following formula (VI).

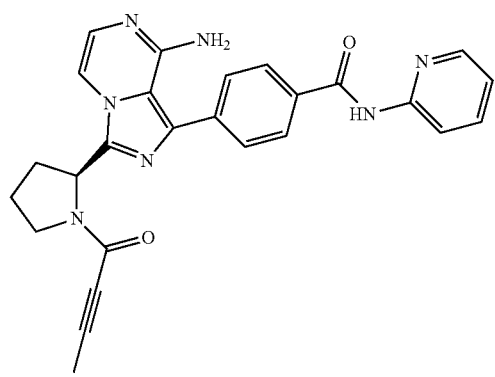

Patent Document CN103889987A reported the preparation of ACP-196 and disclosed liquid chromatography mass spectrometry (LCMS) data of ACP-196. The present inventors have found that ACP-196 obtained according to the preparation method in Example 6 of CN103889987A is a yellow amorphous material which has the disadvantages including solid form instability, susceptible to moisture absorption, poor flowability, and low solubility. Patent document CN103889987A also mentioned that physical forms such as amorphous form, various crystalline forms and salt forms are within the scope of protection thereof, but the patent does not provide characteristic data of any of these physical forms and therefore cannot be treated as fully disclosed.

In view of the disadvantages in the prior art, it is necessary to develop crystalline ACP-196 salts and their crystalline forms with more advantageous properties to meet the strict requirements in pharmaceutical formulations on morphology, solubility, stability and other physicochemical properties of active substances.

SUMMARY OF THE INVENTION

According to the defects of the prior art, the purpose of the present invention is to provide new crystalline forms of ACP-196 salts, and their preparation methods, pharmaceutical compositions and uses thereof. ACP-196 salt forms of the present invention have one or more improved properties, especially in the aspects of crystallinity, hygroscopicity, solubility, stability and formulation processability.

According to a purpose of the present invention, the first aspect of the invention is to provide a solid-state ACP-196 malate Form 1 and its preparation method.

ACP-196 malate Form 1 of the present invention is formed by ACP-196 and malic acid in the molar ratio of 1:1 with its structure shown in the formula (I) below:

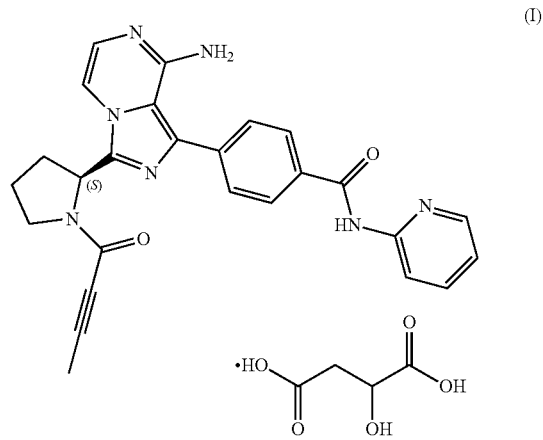

Using Cu-Kα radiation, the X-ray powder diffraction pattern of ACP-196 malate Form 1, expressed as 2θ angles, has the following characteristic peaks: 6.2°±0.2°, 8.90±0.2°, 12.0°±0.2°, 12.4°±0.2°, 16.9°±0.2° and 22.90±0.2°.

In a preferred embodiment of the present invention, the X-ray powder diffraction pattern of ACP-196 malate Form 1, expressed as 2θ angles, has the following characteristic peaks: 6.20±0.2°, 8.90±0.2°, 12.0°±0.2°, 12.4°±0.2°, 15.6°±0.2°, 16.9°±0.2°, 19.6°±0.2°, 20.3°±0.2°, 20.7°±0.2°, 22.9°±0.2°, 23.80±0.2° and 27.60±0.2°.

In a further preferred embodiment of the present invention, the X-ray powder diffraction pattern of ACP-196 malate Form 1, expressed as 2θ angles, has the following characteristic peaks and relative intensities:

| Diffraction angel 2θ | Relative intensity % |
| --- | --- |
| 6.2° ± 0.2° | 81.9 |
| 8.9° ± 0.2° | 21.3 |
| 12.0° ± 0.2° | 70.1 |
| 12.4° ± 0.2° | 100.0 |
| 12.9° ± 0.2° | 8.7 |
| 15.6° ± 0.2° | 12.5 |
| 16.9° ± 0.2° | 22.5 |
| 17.9° ± 0.2° | 10.9 |
| 18.7° ± 0.2° | 7.7 |
| 19.6° ± 0.2° | 21.5 |
| 20.3° ± 0.2° | 16.3 |
| 20.7° ± 0.2° | 16.9 |

-continued

| Diffraction angel 2θ | Relative intensity % |
|---|---|
| 21.2° ± 0.2° | 10.7 |
| 22.9° ± 0.2° | 32.7 |
| 23.8° ± 0.2° | 28.8 |
| 24.9° ± 0.2° | 12.1 |
| 26.3° ± 0.2° | 9.7 |
| 27.6° ± 0.2° | 17.6 |

Non-restrictively, in one typical embodiment of the present invention, the X-ray powder diffraction pattern of ACP-196 malate Form 1 is shown in FIG. 5.

Non-restrictively, the TGA thermogram of ACP-196 malate Form 1 is shown in FIG. 6.

Non-restrictively, the DSC thermogram of ACP-196 malate Form 1 is shown in FIG. 7.

Non-restrictively, the PLM plot of ACP-196 malate Form 1 is shown in FIG. 8.

Non-restrictively, the isothermal sorption plot of ACP-196 malate Form 1 is shown in FIG. 9.

Compared with the known amorphous ACP-196, ACP-196 malate Form 1 has the following beneficial properties:

1) According to the XRPD pattern and PLM plot, ACP-196 malate Form 1 is a crystalline solid with high crystallinity and good stability.

2) According to the isothermal sorption plot, the weight change of ACP-196 malate Form 1 is 1.5% between 30 to 80% RH, while the weight change of amorphous ACP-196 in the same humidity range is 5.5%. ACP-196 malate Form 1 is less hygroscopic.

3) According to Comparative Example 1, ACP-196 malate Form 1 has a higher solubility than amorphous ACP-196.

The above advantageous properties of ACP-196 malate Form 1 show that, compared with the known amorphous ACP-196, ACP-196 malate Form 1 has many advantages and is more suitable for being used as the solid form of the active ingredient in pharmaceutical formulations. The amorphous material is prone to crystallize under the influences of external factors. Such instability may further affect the quality and stability of the pharmaceutical formulations. ACP-196 malate Form 1 is crystalline, and its solid form stability is obviously better (than that of amorphous solids). Crystalline solids usually have better flowability and processing (such as filtrating, drying, weighing, and screening) characteristics, which are beneficial in improving the homogeneity of active ingredients and pharmaceutical formulations. In addition, ACP-196 malate Form 1 has high solubility and better bioavailability, and also has lower hygroscopicity which may better ensure the quality of the active ingredients and formulations containing ACP-196 malate Form 1, avoiding and reducing quality issues, safety issues and stability issues during pharmaceutical production and/or storage, such as content uniformity and impurity issues, avoiding special and expensive package.

The present invention provides preparation methods of ACP-196 malate Form 1, which comprise any one of the following preparation methods:

1) Dissolving ACP-196 and malic acid respectively in a solvent to form solutions, then mixing and stirring for crystallization and precipitation, and then separating crystals and drying to obtain ACP-196 malate Form 1;

preferably, ACP-196 and malic acid use the same solvent to form solutions;

preferably, the solvent is selected from the group consisting of alcohols and ketones, more preferably isopropanol;

preferably, the weight to volume ratio of ACP-196 to solvent when the solution is formed is from 30 mg/mL to 100 mg/mL, more preferably from 30 mg/mL to 50 mg/mL;

preferably, the molar ratio of ACP-196 to malic acid is from 1:0.8 to 1:1.1;

preferably, the stirring time is 1 day to 2 days;

preferably, the operation is carried out at room temperature.

2) Forming a solution of a mixture of ACP-196 and malic acid in a co-solvent, adding anti-solvent, stirring for crystallization and precipitation, and then separating crystals and drying to obtain ACP-196 malate Form 1;

preferably, the co-solvent is selected from the group consisting of ethyl acetate, isopropyl acetate, tetrahydrofuran, 1,4-dioxane, acetonitrile, dichloromethane and chloroform, more preferably tetrahydrofuran;

preferably, the weight to volume ratio of ACP-196 to co-solvent is from 20 mg/mL to 100 mg/mL, more preferably from 20 mg/mL to 50 mg/mL;

preferably, the molar ratio of ACP-196 to malic acid is from 1:0.8 to 1:1.1;

preferably, the anti-solvent is selected from the group consisting of ethers, alkanes and toluene, more preferably isopropyl ether;

preferably, the stirring time is from 1 day to 3 days;

preferably, the operation is carried out at room temperature.

According to a purpose of the present invention, the second aspect of the invention is to provide a solid-state ACP-196 hemifumarate Form 1 and its preparation method.

ACP-196 hemifumarate Form 1 of the present invention is formed by ACP-196 and fumaric acid in the molar ratio of 2:1 with its structure shown in the formula (II) below:

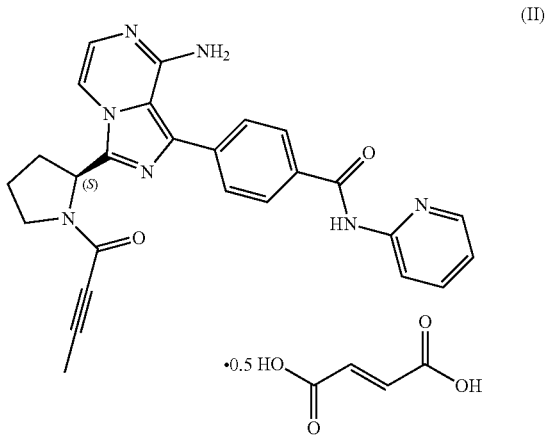

Using Cu-Kα radiation, the X-ray powder diffraction pattern of ACP-196 hemifumarate Form 1, expressed as 2θ angles, has the following characteristic peaks: 4.9°±0.2°, 9.8°±0.2°, 10.8°±0.2°, 11.6°±0.2°, 16.1°+0.2° and 24.9°+0.2°.

In a preferred embodiment of the present invention, the X-ray powder diffraction pattern of ACP-196 hemifumarate Form 1, expressed as 2θ angles, has the following characteristic peaks: 4.9°±0.2°, 7.1°±0.2°, 9.8°+0.2°, 10.8°+0.2°, 11.6°+0.2°, 12.2°+0.2°, 16.1°±0.2°, 20.2°±0.2°, 22.0°±0.2°, 23.2°±0.2°, 24.9°±0.2° and 28.2°+0.2°.

In a further preferred embodiment of the present invention, the X-ray powder diffraction pattern of ACP-196 hemifumarate Form 1, expressed as 2θ angles, has the following characteristic peaks and relative intensities:

| Diffraction angel 2θ | Relative intensity % |
|---|---|
| 4.9° ± 0.2° | 69.2 |
| 5.5° ± 0.2° | 28.4 |
| 7.1° ± 0.2° | 29.0 |
| 9.8° ± 0.2° | 32.8 |
| 10.8° ± 0.2° | 43.3 |
| 11.6° ± 0.2° | 100.0 |
| 12.2° ± 0.2° | 16.2 |
| 16.1° ± 0.2° | 66.8 |
| 18.5° ± 0.2° | 13.8 |
| 20.2° ± 0.2° | 33.1 |
| 22.0° ± 0.2° | 26.5 |
| 23.2° ± 0.2° | 22.0 |
| 24.9° ± 0.2° | 34.3 |
| 26.9° ± 0.2° | 26.3 |
| 28.2° ± 0.2° | 29.4 |

Non-restrictively, in one typical embodiment of the present invention, the X-ray powder diffraction pattern of ACP-196 hemifumarate Form 1 is shown in FIG. 10.

Non-restrictively, the TGA thermogram of ACP-196 hemifumarate Form 1 is shown in FIG. 11.

Non-restrictively, the DSC thermogram of ACP-196 hemifumarate Form 1 is shown in FIG. 12.

Non-restrictively, the PLM plot of ACP-196 hemifumarate Form 1 is shown in FIG. 13.

Non-restrictively, the isothermal sorption plot of ACP-196 hemifumarate Form 1 is shown in FIG. 14.

Compared with the known amorphous ACP-196, ACP-196 hemifumarate Form 1 has the following beneficial properties:

1) According to the XRPD pattern and PLM plot, ACP-196 hemifumarate Form 1 is a crystalline solid with high crystallinity and good stability.

2) According to the isothermal sorption plot, the weight change of ACP-196 hemifumarate Form 1 is 1.2% between 30 to 80% RH, while the weight change of amorphous ACP-196 in the same humidity range is 5.5%. ACP-196 hemifumarate Form 1 is less hygroscopic.

3) According to Comparative Example 1, ACP-196 hemifumarate Form 1 has a higher solubility than amorphous ACP-196.

The above advantageous properties of ACP-196 hemifumarate Form 1 show that, compared with the known amorphous ACP-196, ACP-196 hemifumarate Form 1 has many advantages and is more suitable for being used as the solid form of the active ingredient in pharmaceutical formulations. The amorphous material is prone to crystallize under the influences of external factors, which may further affect the quality and stability of the pharmaceutical formulations. ACP-196 malate Form 1 is crystalline, and its solid form stability is obviously better (than that of amorphous solids). Crystalline solids usually have better flowability and processing (such as filtrating, drying, weighing, and screening) characteristics, which are beneficial in improving the homogeneity of active ingredients and pharmaceutical formulations. In addition, ACP-196 hemifumarate Form 1 has high solubility and better bioavailability, and also has lower hygroscopicity which may better ensure the quality of the active ingredients and formulations containing ACP-196 hemifumarate Form 1, avoiding and reducing quality issues, safety issues and stability issues during pharmaceutical production and/or storage, such as content uniformity and impurity issues, avoiding special and expensive package.

The present invention provides preparation methods of ACP-196 hemifumarate Form 1, which comprise any one of the following preparation methods:

1) Dissolving ACP-196 and fumaric acid respectively in a solvent to form solutions, then mixing and stirring for crystallization and precipitation, and then separating crystals and drying to obtain ACP-196 hemifumarate Form 1;

preferably, ACP-196 and fumaric acid use the same solvent to form solutions;

preferably, the solvent is selected from the group consisting of alcohols and ketones, more preferably acetone;

preferably, the weight to volume ratio of ACP-196 to solvent when the solution is formed is from 40 mg/mL to 200 mg/mL, more preferably from 40 mg/mL to 100 mg/mL;

preferably, the molar ratio of ACP-196 to fumaric acid is from 1:0.5 to 1:1.1;

preferably, the stirring time is 1 day to 2 days;

preferably, the operation is carried out at room temperature.

2) Forming a solution of a mixture of ACP-196 and fumaric acid in a co-solvent, adding anti-solvent, stirring for crystallization and precipitation, and then separating crystals and drying to obtain ACP-196 hemifumarate Form 1;

preferably, the co-solvent is selected from the group consisting of ethyl acetate, isopropyl acetate, tetrahydrofuran, 1,4-dioxane, acetonitrile, dichloromethane and chloroform, more preferably 1,4-dioxane;

preferably, the weight to volume ratio of ACP-196 to co-solvent is from 20 mg/mL to 100 mg/mL, more preferably from 50 mg/mL to 100 mg/mL;

preferably, the molar ratio of ACP-196 to fumaric acid is from 1:0.5 to 1:1.1;

preferably, the anti-solvent is selected from the group consisting of ethers, alkanes and toluene, more preferably isopropyl ether;

preferably, the stirring time is from 1 day to 3 days;

preferably, the operation is carried out at room temperature.

According to a purpose of the present invention, the third aspect of the invention is to provide a solid-state ACP-196 maleate Form 1 and its preparation method.

ACP-196 maleate Form 1 of the present invention is formed by ACP-196 and maleic acid in the molar ratio of 1:1 with its structure shown in the formula (III) below:

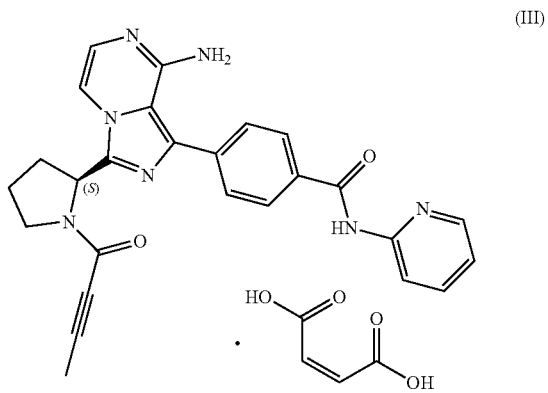

(III)

Using Cu-Kα radiation, the X-ray powder diffraction pattern of ACP-196 maleate Form 1, expressed as 2θ angles, has the following characteristic peaks: 5.3°+0.2° 9.8°±0.2°, 10.5°+0.2°, 11.7°±0.2°, 17.4°±0.2° and 24.4°±0.2°.

In a preferred embodiment of the present invention, the X-ray powder diffraction pattern of ACP-196 maleate Form 1, expressed as 2θ angles, has the following characteristic peaks: 5.3°±0.2°, 9.8°±0.2°, 10.5°±0.2°, 11.7°±0.2°, 15.7°±0.2°, 17.4°±0.2°, 18.8°±0.2°, 19.3°±0.2°, 19.8°±0.2°, 22.8°±0.2°, 24.4°±0.2° and 24.7°±0.2°.

In a further preferred embodiment of the present invention, the X-ray powder diffraction pattern of ACP-196 maleate Form 1, expressed as 2θ angles, has the following characteristic peaks and relative intensities:

| Diffraction angel 2θ | Relative intensity % (I) |
| --- | --- |
| 5.3° ± 0.2° | 36.5 |
| 9.8° ± 0.2° | 27.5 |
| 10.5° ± 0.2° | 100.0 |
| 11.7° ± 0.2° | 97.9 |
| 13.8° ± 0.2° | 11.7 |
| 15.7° ± 0.2° | 23.8 |
| 17.4° ± 0.2° | 47.9 |
| 18.8° ± 0.2° | 20.3 |
| 19.3° ± 0.2° | 29.2 |
| 19.8° ± 0.2° | 19.8 |
| 22.8° ± 0.2° | 31.2 |
| 23.4° ± 0.2° | 20.6 |
| 24.4° ± 0.2° | 61.7 |
| 24.7° ± 0.2° | 43.0 |
| 25.1° ± 0.2° | 24.6 |
| 25.5° ± 0.2° | 9.0 |
| 26.4° ± 0.2° | 13.2 |
| 29.3° ± 0.2° | 12.1 |

Non-restrictively, in one typical embodiment of the present invention, the X-ray powder diffraction pattern of ACP-196 maleate Form 1 is shown in FIG. 15.

Non-restrictively, the TGA thermogram of ACP-196 maleate Form 1 is shown in FIG. 16.

Non-restrictively, the DSC thermogram of ACP-196 maleate Form 1 is shown in FIG. 17.

Non-restrictively, the PLM plot of ACP-196 maleate Form 1 is shown in FIG. 18.

Non-restrictively, the isothermal sorption plot of ACP-196 maleate Form 1 is shown in FIG. 19.

Compared with the known amorphous ACP-196, ACP-196 maleate Form 1 has the following beneficial properties:

1) According to the XRPD pattern and the PLM plot, ACP-196 maleate Form 1 is a crystalline solid with high crystallinity and good stability.

2) According to the isothermal sorption plot, the weight change of ACP-196 maleate Form 1 is 0.4% between 30 to 80% RH, while the weight change of amorphous ACP-196 in the same humidity range is 5.5%. ACP-196 maleate Form 1 is less hygroscopic.

3) According to Comparative Example 1, ACP-196 maleate Form 1 has a higher solubility than amorphous ACP-196.

The above advantageous properties of ACP-196 maleate Form 1 show that, compared with the known amorphous ACP-196, ACP-196 maleate Form 1 has many advantages and is more suitable for being used as the solid form of the active ingredient in pharmaceutical formulations. The amorphous material is prone to crystallize under the influences of external factors, which may further affect the quality and stability of the pharmaceutical formulations. ACP-196 maleate Form 1 is crystalline, and its solid form stability is obviously better (than that of amorphous solids). Crystalline solids usually have better flowability and processing (such as filtrating, drying, weighing, and screening) characteristics, which are beneficial in improving the homogeneity of active ingredients and pharmaceutical formulations. In addition, ACP-196 maleate Form 1 has high solubility and better bioavailability, and also has lower hygroscopicity which may better ensure the quality of the active ingredients and formulations containing ACP-196 maleate Form 1, avoiding and reducing quality issues, safety issues and stability issues during pharmaceutical production and/or storage, such as content uniformity and impurity issues, avoiding special and expensive package.

The present invention provides preparation methods of ACP-196 maleate Form 1, which comprise any one of the following preparation methods:

1) Dissolving ACP-196 and maleic acid respectively in a solvent to form solutions, then mixing and stirring for crystallization and precipitation, and then separating crystals and drying to obtain ACP-196 maleate Form 1;

preferably, ACP-196 and maleic acid use the same solvent to form solutions;

preferably, the solvent is selected from the group consisting of alcohols and ketones, more preferably isopropanol;

preferably, the weight to volume ratio of ACP-196 to solvent when the solution is formed is from 30 mg/mL to 100 mg/mL, more preferably from 30 mg/mL to 50 mg/mL;

preferably, the molar ratio of ACP-196 to maleic acid is from 1:0.8 to 1:1.1;

preferably, the stirring time is 1 day to 2 days;

preferably, the operation is carried out at room temperature.

2) Forming a solution of a mixture of ACP-196 and maleic acid in a co-solvent, adding anti-solvent, stirring for crystallization and precipitation, and then separating crystals and drying to obtain ACP-196 maleate Form 1;

preferably, the co-solvent is selected from the group consisting of ethyl acetate, isopropyl acetate, tetrahydrofuran, 1,4-dioxane, acetonitrile, dichloromethane and chloroform, more preferably tetrahydrofuran;

preferably, the weight to volume ratio of ACP-196 to co-solvent is from 20 mg/mL to 100 mg/mL, more preferably from 20 mg/mL to 50 mg/mL;

preferably, the molar ratio of ACP-196 to maleic acid is from 1:0.8 to 1:1.1;

preferably, the anti-solvent is selected from the group consisting of ethers, alkanes and toluene, more preferably n-heptane;

preferably, the stirring time is from 1 day to 3 days;

preferably, the operation is carried out at room temperature.

According to a purpose of the present invention, the fourth aspect of the invention is to provide a solid-state ACP-196 phosphate Form 1 and its preparation method.

ACP-196 phosphate Form 1 of the present invention is formed by ACP-196, phosphoric acid and water in the molar ratio of 1:1:1.5 with its structure shown in the formula (IV) below:

(IV)

·H₃PO₄·1.5H₂O

Using Cu-Kα radiation, the X-ray powder diffraction pattern of ACP-196 phosphate Form 1, expressed as 2θ angles, has the following characteristic peaks: 4.5°±0.2°, 10.4°±0.2°, 12.0°±0.2°, 14.3°±0.2°, 18.0°+0.2° and 21.9°+0.2°.

In a preferred embodiment of the present invention, the X-ray powder diffraction pattern of ACP-196 phosphate Form 1, expressed as 2θ angles, has the following characteristic peaks: 4.5°±0.2°, 6.0°±0.2°, 10.4°±0.2°, 12.0°±0.2°, 14.3°±0.2°, 15.5°±0.2°, 18.0°±0.2°, 19.3°±0.2°, 20.5°±0.2°, 20.9°±0.2°, 21.9°±0.2° and 25.1°±0.2°.

In a further preferred embodiment of the present invention, the X-ray powder diffraction pattern of ACP-196 phosphate Form 1, expressed as 2θ angles, has the following characteristic peaks and relative intensities:

| Diffraction angel 2θ | Relative intensity % (I) |
|---|---|
| 4.5° ± 0.2° | 39.9 |
| 6.0° ± 0.2° | 40.4 |
| 10.4° ± 0.2° | 91.8 |
| 12.0° ± 0.2° | 94.2 |
| 12.5° ± 0.2° | 22.4 |
| 13.1° ± 0.2° | 26.2 |
| 14.3° ± 0.2° | 92.7 |
| 15.5° ± 0.2° | 31.5 |
| 18.0° ± 0.2° | 75.1 |
| 18.4° ± 0.2° | 31.1 |
| 19.3° ± 0.2° | 77.3 |
| 20.5° ± 0.2° | 32.0 |
| 20.9° ± 0.2° | 45.0 |
| 21.9° ± 0.2° | 100.0 |
| 22.6° ± 0.2° | 25.7 |
| 23.1° ± 0.2° | 26.7 |
| 24.2° ± 0.2° | 30.8 |
| 25.1° ± 0.2° | 44.8 |
| 26.9° ± 0.2° | 28.9 |
| 27.5° ± 0.2° | 24.9 |
| 30.9° ± 0.2° | 22.9 |

Non-restrictively, in one typical embodiment of the present invention, the X-ray powder diffraction pattern of ACP-196 phosphate Form 1 is shown in FIG. 20.

Non-restrictively, the TGA thermogram of ACP-196 phosphate Form 1 is shown in FIG. 21.

Non-restrictively, the DSC thermogram of ACP-196 phosphate Form 1 is shown in FIG. 22.

Non-restrictively, the PLM plot of ACP-196 phosphate Form 1 is shown in FIG. 23.

Non-restrictively, the isothermal sorption plot of ACP-196 phosphate Form 1 is shown in FIG. 24.

Compared with the known amorphous ACP-196, ACP-196 phosphate Form 1 has the following beneficial properties:

1) According to the XRPD pattern and PLM plot, ACP-196 phosphate Form 1 is a crystalline solid with high crystallinity and good stability.

2) According to the isothermal sorption plot, the weight change of ACP-196 phosphate Form 1 is 4.2% between 30 to 80% RH, while the weight change of amorphous ACP-196 in the same humidity range is 5.5%. ACP-196 phosphate Form 1 is less hygroscopic.

3) According to Comparative Example 1, ACP-196 phosphate Form 1 has a higher solubility than amorphous ACP-196.

The above advantageous properties of ACP-196 phosphate Form 1 show that, compared with the known amorphous ACP-196, ACP-196 phosphate Form 1 has many advantages and is more suitable for being used as the solid form of the active ingredient in pharmaceutical formulations. The amorphous material is prone to crystallize under the influences of external factors, which may further affect the quality and stability of the pharmaceutical formulations. ACP-196 phosphate Form 1 is crystalline, and its solid form stability is obviously better (than that of amorphous solids). Crystalline solids usually have better flowability and processing (such as filtrating, drying, weighing, and screening) characteristics, which are beneficial in improving the homogeneity of active ingredients and pharmaceutical formulations. In addition, ACP-196 phosphate Form 1 has high solubility and better bioavailability, and also has lower hygroscopicity which may better ensure the quality of the active ingredients and formulations containing ACP-196 phosphate Form 1, avoiding and reducing quality issues, safety issues and stability issues during pharmaceutical production and/or storage, such as content uniformity and impurity issues, avoiding special and expensive package.

The present invention provides preparation methods of ACP-196 phosphate Form 1, which comprise any one of the following preparation methods:

1) Dissolving ACP-196 and phosphoric acid respectively in a solvent to form solutions, then mixing and stirring for crystallization and precipitation, and then separating crystals and drying to obtain ACP-196 phosphate Form 1;

preferably, ACP-196 and phosphoric acid use the same solvent to form solutions;

preferably, the solvent is selected from the group consisting of alcohols and ketones, more preferably isopropanol;

preferably, the weight to volume ratio of ACP-196 to solvent when the solution is formed is from 30 mg/mL to 100 mg/mL, more preferably from 30 mg/mL to 50 mg/mL;

preferably, the molar ratio of ACP-196 to phosphoric acid is from 1:0.8 to 1:1.1;

preferably, the stirring time is 1 day to 2 days;

preferably, the operation is carried out at room temperature.

2) Forming a solution of ACP-196 in a co-solvent, dropwisely adding phosphoric acid and then adding anti-solvent, stirring for crystallization and precipitation, and then separating crystals and drying to obtain ACP-196 phosphate Form 1;

preferably, the co-solvent is selected from the group consisting of ethyl acetate, isopropyl acetate, tetrahydrofuran, 1,4-dioxane, acetonitrile, dichloromethane and chloroform, more preferably dichloromethane;

preferably, the weight to volume ratio of ACP-196 to co-solvent is from 50 mg/mL to 150 mg/mL, more preferably from 50 mg/mL to 100 mg/mL;

preferably, the molar ratio of ACP-196 to phosphoric acid is from 1:0.8 to 1:1.1;

preferably, the anti-solvent is selected from the group consisting of ethers, alkanes and toluene, more preferably methylcyclohexane;

preferably, the stirring time is from 1 day to 3 days;

preferably, the operation is carried out at room temperature.

According to a purpose of the present invention, the fifth aspect of the invention is to provide a solid-state ACP-196 sulfate Form 1 and its preparation method.

ACP-196 sulfate Form 1 of the present invention is formed by ACP-196 and sulfuric acid in the molar ratio of 1:1 with its structure shown in the formula (V) below:

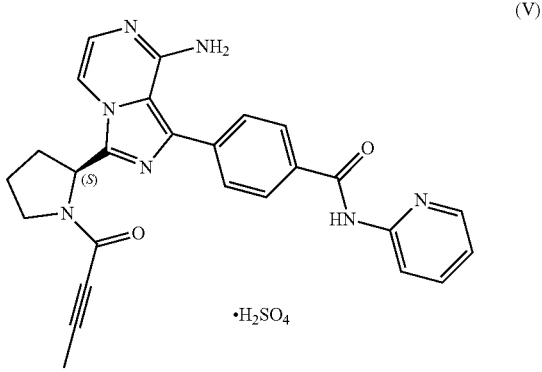

(V)

Using Cu-Kα radiation, the X-ray powder diffraction pattern of ACP-196 sulfate Form 1, expressed as 2θ angles, has the following characteristic peaks: 8.9°±0.2°, 9.7°+0.2°, 17.5°±0.2°, 19.6°±0.2°, 21.9°+0.2° and 23.6°+0.2°.

In a preferred embodiment of the present invention, the X-ray powder diffraction pattern of ACP-196 sulfate Form 1, expressed as 2θ angles, has the following characteristic peaks: 4.6°±0.2°, 7.9°+0.2°, 8.9°±0.2°, 9.7°+0.2°, 14.6°±0.2°, 15.0°±0.2°, 17.5°±0.2°, 19.6°±0.2°, 20.0°±0.2°, 21.9°±0.2°, 23.6°±0.2° and 25.9°±0.2°.

In a further preferred embodiment of the present invention, the X-ray powder diffraction pattern of ACP-196 sulfate Form 1, expressed as 2θ angles, has the following characteristic peaks and relative intensities:

| Diffraction angel 2θ | Relative intensity % |
|---|---|
| 4.6° ± 0.2° | 21.6 |
| 7.9° ± 0.2° | 14.2 |
| 8.9° ± 0.2° | 41.9 |
| 9.7° ± 0.2° | 70.4 |
| 14.6° ± 0.2° | 21.2 |
| 15.0° ± 0.2° | 20.7 |
| 17.5° ± 0.2° | 100.0 |
| 17.8° ± 0.2° | 47.5 |
| 19.6° ± 0.2° | 50.7 |
| 20.0° ± 0.2° | 31.4 |
| 21.9° ± 0.2° | 59.7 |
| 23.6° ± 0.2° | 53.3 |
| 24.3° ± 0.2° | 31.8 |
| 24.8° ± 0.2° | 18.5 |
| 25.6° ± 0.2° | 27.9 |
| 25.9° ± 0.2° | 33.4 |
| 27.1° ± 0.2° | 16.0 |
| 27.5° ± 0.2° | 13.2 |
| 28.0° ± 0.2° | 8.2 |
| 29.2° ± 0.2° | 26.7 |
| 30.2° ± 0.2° | 11.1 |
| 31.6° ± 0.2° | 13.3 |

Non-restrictively, in one typical embodiment of the present invention, the X-ray powder diffraction pattern of ACP-196 sulfate Form 1 is shown in FIG. 25.

Compared with the known amorphous ACP-196, ACP-196 sulfate Form 1 has the following beneficial properties:

1) According to the XRPD pattern and PLM plot, ACP-196 sulfate Form 1 is a crystalline solid with high crystallinity and good stability.

2) According to Comparative Example 1, ACP-196 sulfate Form 1 has a higher solubility than amorphous ACP-196.

The above advantageous properties of ACP-196 sulfate Form 1 show that, compared with the known amorphous ACP-196, ACP-196 sulfate Form 1 has many advantages and is more suitable for being used as the solid form of the active ingredient in pharmaceutical formulations. The amorphous material is prone to crystallize under the influences of external factors, which may further affect the quality and stability of the pharmaceutical formulations. ACP-196 sulfate Form 1 is crystalline, and its solid form stability is obviously better (than that of amorphous solids). Crystalline solids usually have better flowability and processing (such as filtrating, drying, weighing, and screening) characteristics, which are beneficial in improving the homogeneity of active ingredients and pharmaceutical formulations, and may better ensure the quality of the active ingredients and formulations containing ACP-196 sulfate Form 1, avoiding and reducing quality issues, safety issues and stability issues during pharmaceutical production and/or storage, such as content uniformity and impurity issues, avoiding special and expensive package. ACP-196 sulfate Form 1 has high solubility and better bioavailability.

The present invention provides preparation methods of ACP-196 sulfate Form 1, which comprise any one of the following preparation methods:

1) Dissolving ACP-196 and sulfuric acid respectively in a solvent to form solutions, then mixing and stirring for crystallization and precipitation, and then separating crystals and drying to obtain ACP-196 sulfate Form 1;

preferably, ACP-196 and sulfuric acid are selected from the same solvent to form a solution;

preferably, the solvent is selected from the group consisting of alcohols and ketones, more preferably isopropanol;

preferably, the weight to volume ratio of ACP-196 to solvent when the solution is formed is from 30 mg/mL to 100 mg/mL, more preferably from 30 mg/mL to 50 mg/mL;

preferably, the molar ratio of ACP-196 to sulfuric acid is from 1:0.8 to 1:1.1;

preferably, the stirring time is 1 day to 2 days;

preferably, the operation is carried out at room temperature.

2) Forming a solution of ACP-196 in a co-solvent, dropwisely adding sulfuric acid and then adding anti-solvent, stirring for crystallization and precipitation, and then separating crystals and drying to obtain ACP-196 sulfate Form 1;

preferably, the co-solvent is selected from the group consisting of ethyl acetate, isopropyl acetate, tetrahydrofuran, 1,4-dioxane, acetonitrile, dichloromethane and chloroform, more preferably ethyl acetate;

preferably, the weight to volume ratio of ACP-196 to co-solvent is from 10 mg/mL to 50 mg/mL, more preferably from 25 mg/mL to 50 mg/mL;

preferably, the molar ratio of ACP-196 to sulfuric acid is from 1:0.8 to 1:1.1;

preferably, the anti-solvent is selected from the group consisting of ethers, alkanes and toluene, more preferably n-hexane;

preferably, the stirring time is from 1 day to 3 days;

preferably, the operation is carried out at room temperature.

In the preparation methods of the crystalline forms of ACP-196 salts of the present invention, the starting material "ACP-196" may be a disclosed ACP-196 compound including an amorphous ACP-196, for example, but not limited to, ACP-196 prepared according to any one of the preparation methods in patent document CN103889987A. These patent documents are incorporated herein by reference in their entirety.

The terms used in the present invention include:

The "room temperature" is a temperature between 10° C. and 30° C.

"Stirring" may be carried out by a conventional stirring method in the field, such as magnetic stirring, mechanical stirring, and the stirring speed is 50 to 1800 r/min, preferably 300 to 900 r/min.

"Separating" may be performed using conventional methods in the field, such as vacuum concentration, volatilization, centrifugation or filtration. Preferred method is vacuum filtration or vacuum concentration, generally at a pressure less than atmospheric pressure at room temperature, preferably less than 0.09 MPa.

"Drying" may be performed by routine methods in the field, such as room temperature drying, forced air drying or vacuum drying. Drying is performed under reduced pressure or atmospheric pressure, and pressure less than 0.09 MPa is preferred. Drying instruments and methods are unrestricted, and may be fume hood, blast oven, spray drying, fluidized bed drying or vacuum oven.

In the present invention, "crystal" or "crystalline form" refers to that characterized by X-ray powder diffraction pattern, having a unique ordered molecular arrangement or configuration within the crystalline lattice. It is known to those skilled in the field that the experimental error depends on instrumental conditions, sample preparation and sample purity. The 2θ angle of the peaks in the XRPD pattern may change with the change of instrument and samples. The difference of peak position may vary by 1°, 0.8°, 0.5°, 0.3°, 0.10, etc., depending on the instruments and samples, and +0.2° in error is usually allowed. Therefore the difference in peak position should not be regarded as the only factor. The relative intensity of peaks may change with the change of sample, sample preparation, and other experimental conditions. Therefore, the order of peak intensities should not be regarded as the only or the determining factor. Due to the effect of experimental factors including sample height, peak position may shift. Generally, a small amount of peak shifting is acceptable. Hence, it is easily understood for those skilled in the field that any crystalline form having the same or similar X-ray powder diffraction pattern as that of the crystalline form in the present invention should be within the scope of the present invention. "Single crystalline form" refers to a crystalline form confirmed by X-ray powder diffraction as a single form.

The crystalline forms of ACP-196 salts of the present invention are substantially pure, single, or substantially free of any other crystalline or amorphous forms. As used herein, "substantially pure" when used in reference to a new crystalline form means that the new crystalline form comprises at least 80% by weight of the present compound, more preferably at least 90% (by weight), especially at least 95% (by weight), especially at least 99% (by weight).

The sixth aspect of the invention is to provide a pharmaceutical composition, which comprises a therapeutically and/or preventively effective amount of pharmaceutical active ingredient selected from the crystalline forms of ACP-196 salts of the present invention or the crystalline forms of ACP-196 salts prepared by the preparation methods of the present invention, and at least one pharmaceutically acceptable excipient or carrier. Wherein the crystalline forms of ACP-196 salts of the present invention include ACP-196 malate Form 1, ACP-196 hemifumarate Form 1, ACP-196 maleate Form 1, ACP-196 phosphate Form 1 and ACP-196 sulfate Form 1. In addition, the pharmaceutical composition may also comprise other pharmaceutically acceptable salts, crystalline forms or amorphous forms of ACP-196. The dosage form of the compound used in the method of the present invention may be determined by selecting specific solid state of the compound, the type of pharmacokinetic distribution required by the route of administration and the status of the patient.

The compound of the present invention may be formulated for oral, sublingual, subcutaneous, intravenous, intramuscular, nasal, topical or rectal administration according to generally accepted methods in the pharmaceutical field, and the formulations contain at least one active compound, preferably in the form of a unit dosage form for administration. The human dose preferably contains 0.001 to 25 mg/kg body weight.

The pharmaceutical composition may be prepared as a certain dosage form depending on the route of administration or need, and may be solid or liquid. Solid oral dosage forms, include, for example, tablets, granules, powders, pills, and capsules; liquid oral dosage forms, include, for example, solutions, syrups, suspensions, dispersions, and emulsions; injectables includes, for example, solutions, dispersions and lyophilized products. The formulation may be suitable for immediate, sustained or controlled release of the active ingredient of the drug. It may be a conventional, dispersible, chewable, buccal soluble or rapidly dissolvable formulation.

The excipients of pharmaceutical composition are known to those skilled in the field, and the selection of the type, usage and amount of the excipients is also known to those skilled in the field. For example, they include carbohydrate, cellulose and its derivative, starch or modified starch, solid inorganics such as calcium phosphate, dicalcium phosphate, hydroxyapatite, calcium sulfate, calcium carbonate, semisolid such as lipids or paraffin wax, adhesives such as microcrystalline cellulose, ethyl cellulose, hydroxymethyl cellulose, hydroxypropyl methyl cellulose, hydroxyethyl cellulose, glidants such as colloidal silica dioxide, light anhydrous silicic acid, crystalline cellulose, talcum powder or magnesium stearate, disintegrants such as sodium glycolate starch, crospovidone, croscarmellose, sodium carboxymethylcellulose, cornstarch, lubricant such as stearic acid, magnesium stearate, sodium stearyl fumarate, polyethyleneglycol.

For making solid dosage units, the use of conventional additives such as filters, colorants, adhesives and the like is expected. In general any inactive pharmaceutically acceptable carriers can be used. the active ingredient of the present invention can be administered together with these carriers as solid compositions. Suitable carriers include lactose, starch, sucrose, glucose, methyl cellulose, or mixtures thereof, and can be used in suitable amount. For parenteral administration, aqueous suspensions, isotonic saline solutions and sterile injectable solutions containing pharmaceutically acceptable dispersing agents and/or wetting agents, such as propylene glycol or butylene glycol can be used.

The pharmaceutical composition may be prepared by the method commonly known to those skilled in the art. In preparation of the pharmaceutical composition, the crystalline forms of ACP-196 salts of the present invention (including ACP-196 malate Form 1, ACP-196 hemifumarate Form 1, ACP-196 maleate Form 1, ACP-196 phosphate Form 1 and ACP-196 sulfate Form 1) are mixed with one or more pharmaceutically acceptable excipients, optionally with other pharmaceutically acceptable polymorphs, salt forms and amorphous form of ACP-196, optionally with one or more other active ingredients. Solid formulations may be prepared by direct mixing, granulation and other processes.

For oral administration, the active ingredient may be presented as discrete units, such as tablets, capsules, powders, granulates, solutions, suspensions, etc.

For parenteral administration, the pharmaceutical composition of the present invention may be presented in unit-dose or multidose containers, e.g. injection liquids in predetermined amounts, for example in sealed vials and ampoules, and may be stored in a freeze dried (lyophilized) condition.

According to the purpose of the present invention, the seventh aspect of the present invention provides crystalline forms of ACP-196 salts or the crystalline forms of ACP-196 salts prepared by the preparation methods of the present invention for the preparation of drugs for the treatment or prevention of tyrosine kinases such as Bruton tyrosine kinase (BTK) mediated diseases or conditions. The crystalline forms of ACP-196 salts of the present invention include ACP-196 malate Form 1, ACP-196 hemifumarate Form 1, ACP-196 maleate Form 1, ACP-196 phosphate Form 1 and ACP-196 sulfate Form 1. The disease or condition mediated by BTK refers to any disease or other harmful condition in which B cells, mast cells, myeloid cells or osteoclasts play a major role. These diseases include, but are not limited to, immune, autoimmune and inflammatory diseases, allergies, infectious diseases, bone resorption diseases and proliferative diseases. The immune, autoimmune and inflammatory diseases described include, but are not limited to, such as arthritis, rheumatoid arthritis, psoriatic arthritis, osteoarthritis, infective arthritis, infectious arthritis, progressive chronic arthritis, teratogenic arthritis, ankylosing spondylitis, juvenile rheumatoid arthritis, traumatic arthritis, gouty arthritis, Reiter's syndrome, autoimmune Addison's disease, polychondritis, acute synovitis and spondylitis etc., glomerulonephritis, autoimmune blood system disorders such as autoimmune hemolytic anemia, aplastic anemia, autoimmune thrombocytopenic purpura (ATP), autoimmune lymphocytosis syndrome (ALPS), and neutropenia, autoimmune hepatitis, autoimmune gastritis and autoimmune inflammatory bowel diseases (such as ulcerative colitis and Crohn's disease), graft-versus-host disease, homology allograft rejection, thyroid dysfunction, Hashimoto thyroiditis, Graves' disease, scleroderma, diabetes (type I and II), active hepatitis (acute and chronic), pancreatitis, primary biliary cirrhosis, acquired immunodeficiency syndrome (AIDS), endometriosis, myasthenia gravis, chronic fatigue immune syndrome (CFIDS), pernicious anemia, nodular polyarteritis, polychondritis, polygland syndrome, rheumatic polymyopathy, polymyositis and dermatomyositis, primary agammaglobulinemia, autoimmune inner ear disease (AIED), multiple sclerosis, lupus, psoriasis, psoriatic arthritis, atopic dermatitis, contact dermatitis, eczema, papules, rheumatic fever, skin sunburn, vasculitis (e.g. Behcet's disease), chronic renal insufficiency, Stevens-Johnson syndrome, inflammatory pain, idiopathic sprue, cachexia, sarcoidosis, juvenile dermatomyositis, infectious neuropathy (Guillain-Barré syndrome), uveitis, vitiligo, granuloma, conjunctivitis, keratoconjunctivitis, otitis media, fibromyositis, periodontitis, pulmonary interstitial fibrosis, asthma, appendix inflammation, bronchiolitis, bronchitis, rhinitis, sinusitis, pneumoconiosis, pulmonary insufficiency syndrome, emphysema, pulmonary fibrosis, silicosis, chronic inflammatory pulmonary disease (such as chronic obstructive pulmonary disease) and other inflammatory or obstructive diseases of the respiratory tract.

Allergies that can be treated or prevented include, for example, allergies to food, food additives, insect toxins, molds, dust mites, pollen, animal materials, drugs and metals, type I hypersensitivity, allergic asthma, allergic rhinitis, allergies conjunctivitis or atopic dermatitis.

Infectious diseases that can be treated or prevented include, but are not limited to, for example, sepsis, septic shock, endotoxic shock, sepsis caused by gram-negative bacteria, shigella, meningitis, pleurisy, malaria, pneumonia, bronchi inflammation, tuberculosis, endocarditis, viral myocarditis, viral hepatitis (hepatitis A, hepatitis B and hepatitis C), nephritis, HIV infection, tendinitis, retinitis, influenza, herpes, measles, whooping cough, enteritis, infections associated with severe burns, myalgia caused by infection, cachexia caused by infection, and infection caused by animal viruses.

Bone resorption diseases and conditions that can be treated or prevented include, for example, osteoporosis, osteoarthritis, traumatic arthritis, gouty arthritis, and bone disorders associated with multiple myeloma.

Proliferative diseases that can be treated or prevented include, for example, B cell proliferative diseases such as diffuse large B cell lymphoma, mantle cell lymphoma (MCL), follicular lymphoma, chronic lymphocytic lymphoma, chronic lymphocytic leukemia, B cell pro-lymphocytic leukemia, acute lymphocytic leukemia (ALL), lymphoplasmacytic lymphoma/Waldenstrom macroglobulinemia, marginal lymphoma, hairy cell leukemia, plasma cell myeloma, plasmacytoma, extranodal marginal zone B cell lymphoma, lymph node marginal zone B cell lymphoma, diffuse mixed cell and large cell lymphoma, mediastinal (thymus) large B cell lymphoma, intravascular large B cell lymphoma, primary exudative lymphoma, Burkitt lymphoma/leukemia or lymphomatoid granulomatosis, and AIDS-related lymphoma. The crystalline forms of the compounds of the present invention especially may be used for the treatment of B cell lymphomas caused by chronic active B cell receptor signaling.

According to the object of the invention, a method of treating and/or preventing a Bruton's tyrosine kinase (BTK) mediated disease, comprising administering to a patient in need thereof a prophylactically, inhibitory and/or therapeutically effective amount of one or more of ACP-196 malate Form 1 or ACP-196 hemifumarate Form 1 or ACP-196 maleate Form 1 or ACP-196 phosphate Form 1 or ACP-196 sulfate Form 1 of the present invention, or a pharmaceutical composition containing one or more of ACP-196 malate Form 1 or ACP-196 hemifumarate Form 1 or ACP-196 maleate Form 1 or ACP-196 phosphate Form 1 or ACP-196 sulfate Form 1 of the present invention; the disease is described in the specification section of the present invention. The effective amount, for example, a human dose for parenteral administration, preferably contains from 0.001 to 25 mg/kg body weight. The desired dose can be presented as a single dose or as multiple sub-doses administered at appropriate intervals throughout the day.

SPECIFIC IMPLEMENTATIONS

The following examples will help to further understand the present invention, but are not intended to limit the contents of the present invention.

Instruments and Characterization Methods:

X-ray powder diffraction (XRPD): performed on Bruker D8 Advance diffractometer. Samples were tested at room temperature. Testing conditions: 2θ scan range 3-40°, step size 0.02°, and speed 0.2 s/step.

Polarized light microscopy (PLM) plots were collected on XP-500E polarized light microscopy. Took a small amount of powder sample on a glass and added some mineral oil, covered with the cover glass, placed it on the stage for observation and took a picture.

Differential thermal analysis data were collected on TA Instruments Q200 DSC. Method: A sample of 1 to 10 mg was placed in an aluminum pan with a pin-holed lid, and the sample was heated from room temperature to 200° C. at a heating rate of 10° C./min under the protection of dry nitrogen purge at 40 mL/min.

Thermogravimetric analysis data were collected on TA Instruments Q500 TGA. Method: A sample of 5 to 15 mg was placed in a platinum pan, using High Resolution™, the sample was heated from room temperature to 350° C. at a heating rate of 10° C./min under the protection of dry nitrogen purge at 40 mL/min.

Dynamic vapor sorption data and isothermal sorption data were collected on TA Instruments Q5000 TGA. Method: A sample of 1 to 10 mg was placed in a platinum pan; the weight change of the sample during the change in relative humidity from 0% to 80% to 0% was measured.

1H Nuclear magnetic resonance spectrum ($^1$H-NMR) data were collected on Bruker Avance II DMX 500 MHz nuclear magnetic resonance spectrometer. Method: place 1 mg to 10 mg sample and dissolve it into a nuclear magnetic sample tube with 0.5 mL deuterated reagent for detection.

Ion chromatograph (IC) data were collected on Dionex ICS-900. The workstation and analysis software are Chromeleon Console. Ion content was determined by external standard method.

Unless particularly specified, all reagents used in the Examples were commercially available.

Unless particularly specified, all Examples were operated at room temperature.

Preparation Example 1

Prepare ACP-196

The ACP-196 prepared by referencing the methods described in Example 6 of patent document CN103889987A. Data: LCMS(B)Rt: 2.08 min; m/z 466.1 (M+H)+.

Figure 1:
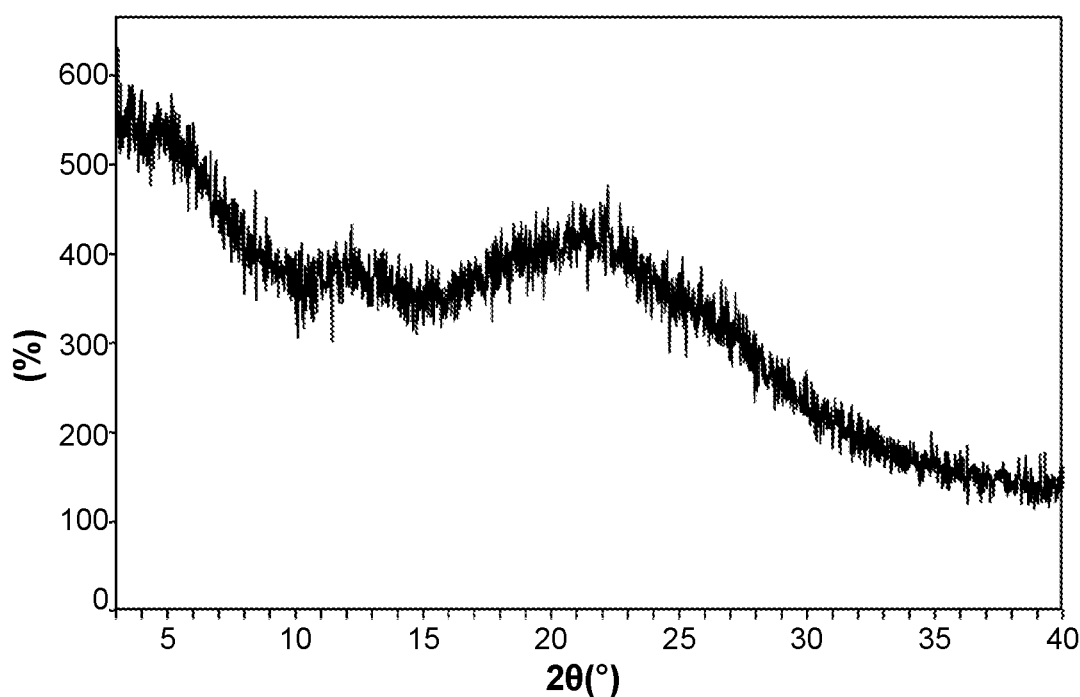
FIG. 1 is the XPRD pattern of amorphous ACP-196 prepared according to CN103889987A.

Its XRPD pattern is shown in FIG. 1, showing no diffraction peaks.

Figure 2:
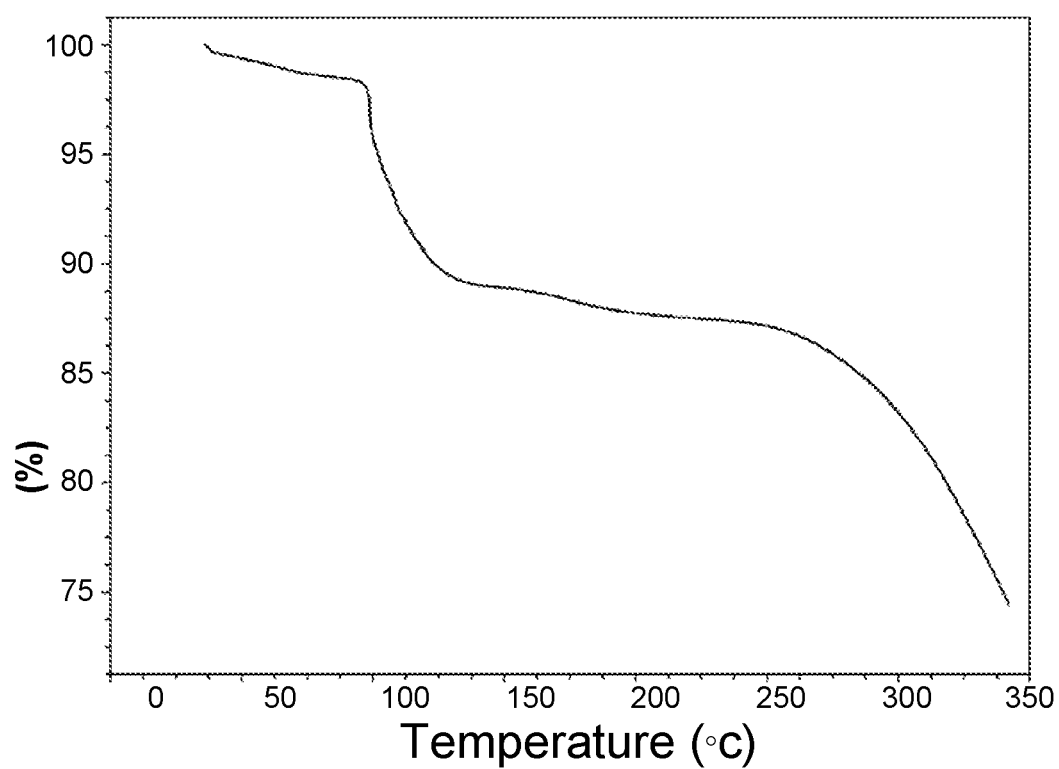
FIG. 2 is the TGA thermogram of amorphous ACP-196 prepared according to CN103889987A.

Its TGA thermogram is shown in FIG. 2, showing more than 10% surface solvent.

Figure 3:
FIG. 3 is the PLM plot of amorphous ACP-196 prepared according to CN103889987A.

Its PLM plot is shown in FIG. 3, showing irregular particles with no polarization.

Figure 4:
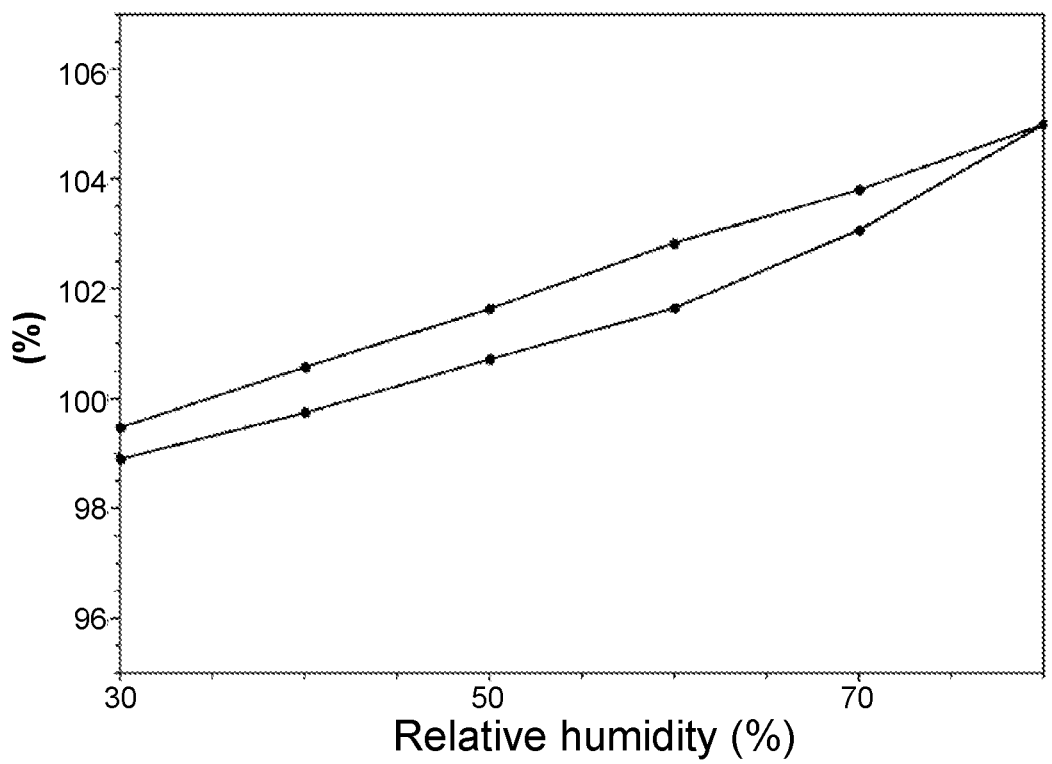
FIG. 4 is the isothermal sorption plot of amorphous ACP-196 prepared according to CN103889987A.

Its isothermal sorption plot is shown in FIG. 4, showing a weight change of 5.5% in the range of 30% to 80% relative humidity.

The above characterization results indicate that ACP-196 obtained by the method described in Example 6 of patent document CN100352817A is an amorphous substance.

Example 1

Placed 3 g ACP-196 of Preparation Example 1 in 100 mL isopropanol to form a solution, slowly and dropwisely added 50 mL isopropanol solution containing malic acid (1.1 eq), stirred for 2 days for crystallization and precipitation, filtrated, and then vacuum dried at room temperature for 24 hours to obtain 3.3 g ACP-196 malate Form 1; 85% yield.
$^1$H-NMR (d6-DMSO, 500 MHz): 10.84 (s, 1H), 8.50-8.34 (m, 1H), 8.32-8.08 (m, 2H), 7.87 (td, 3H), 7.26-7.04 (m, 2H), 6.22 (s, 2H), 5.73 (dd, 1H), 5.49 (dd, 1H), 4.26 (s, 1H), 3.84 (t, 1H), 3.62 (dtt, 1H), 2.62 (dd, 1H), 2.48-2.18 (m, 3H), 2.15 (dt, 1H), 2.08-1.92 (m, 2H), 1.64 (s, 1H).

The result showed that ACP-196 and malic acid formed a salt at a molar ratio of about 1:1.

Figure 5:
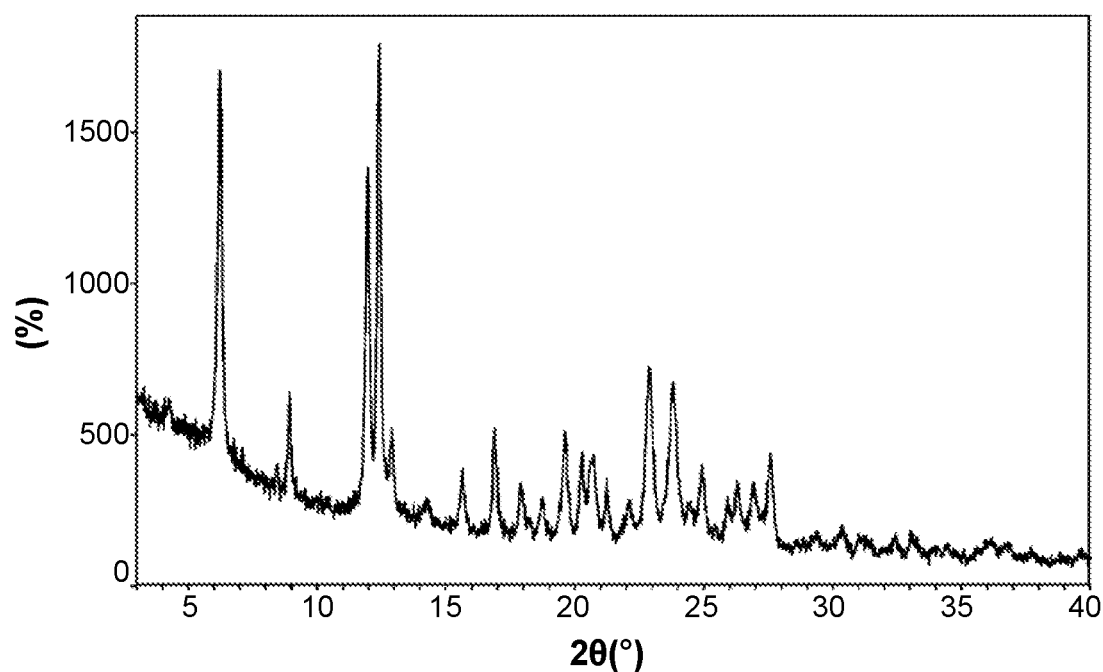
FIG. 5 is the XRPD pattern of ACP-196 malate Form 1 prepared by the present invention.

Its XRPD pattern is shown in FIG. 5, showing it was crystalline.

Figure 6:
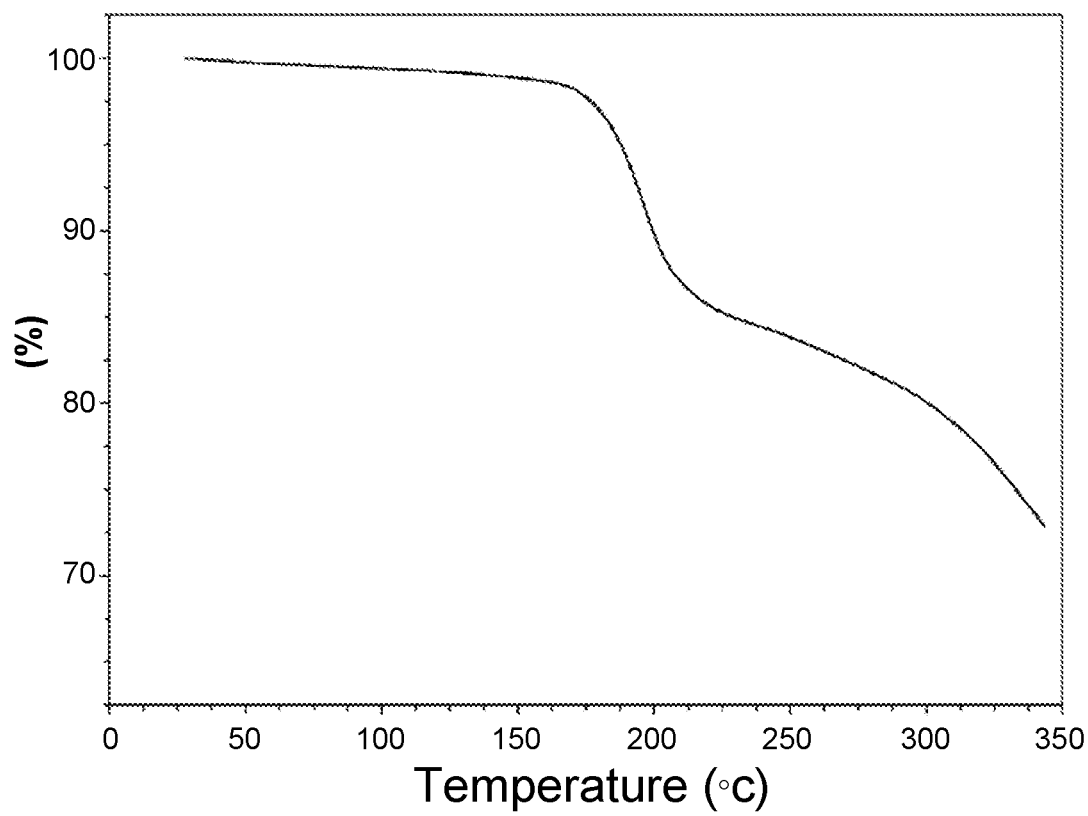
FIG. 6 is the TGA thermogram of ACP-196 malate Form 1 prepared by the present invention.

Its TGA thermogram is shown in FIG. 6, showing an anhydrate with a decomposition temperature at about 181° C.

Figure 7:
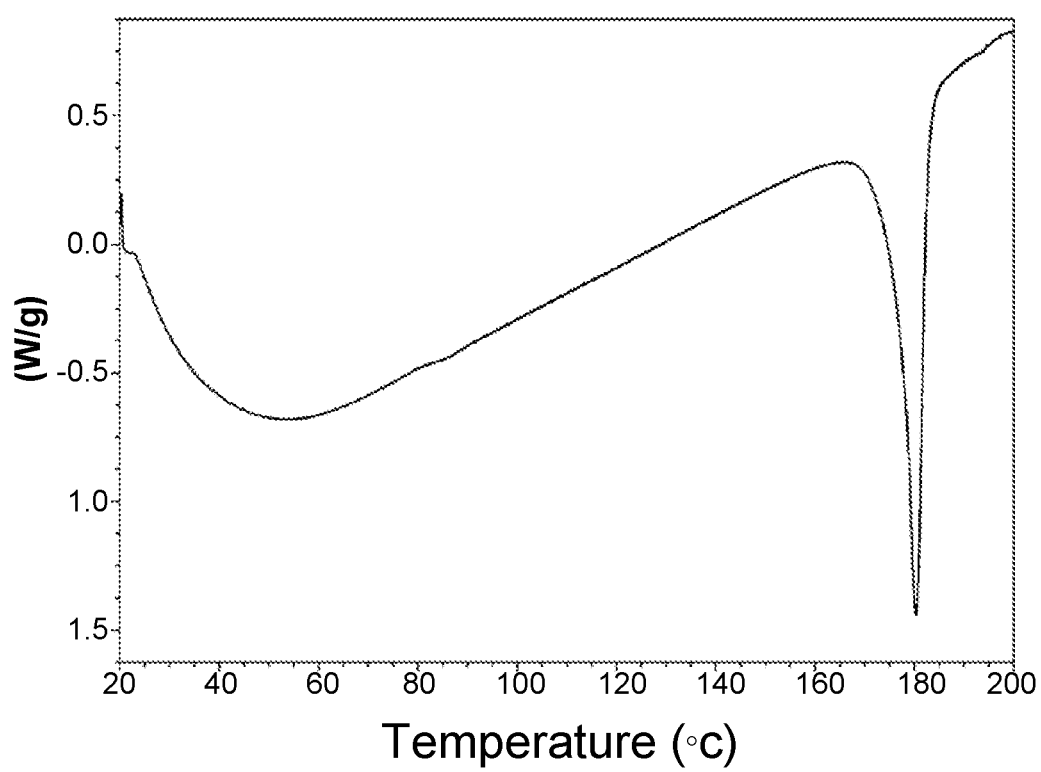
FIG. 7 is the DSC thermogram of ACP-196 malate Form 1 prepared by the present invention.

Its DSC thermogram is shown in FIG. 7, showing a melting point at about 177° C.

Figure 8:
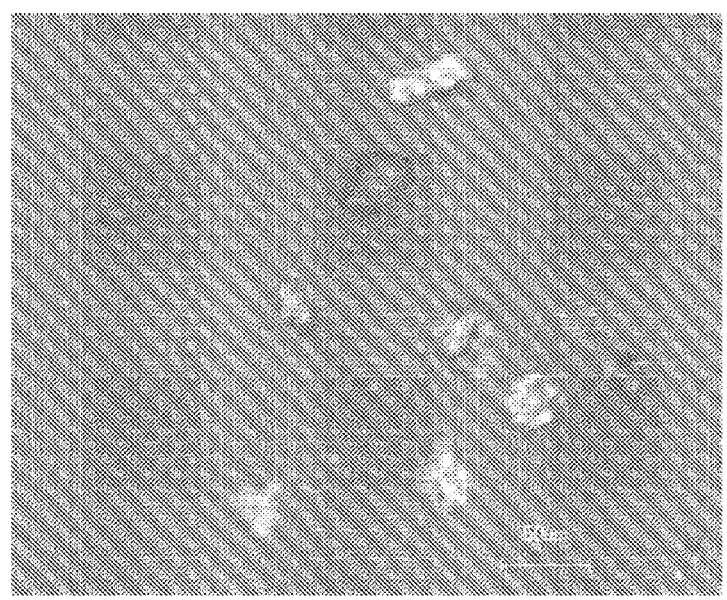
FIG. 8 is the PLM plot of ACP-196 malate Form 1 prepared by the present invention.

Its PLM pattern is shown in FIG. 8, showing regular block particles.

Figure 9:
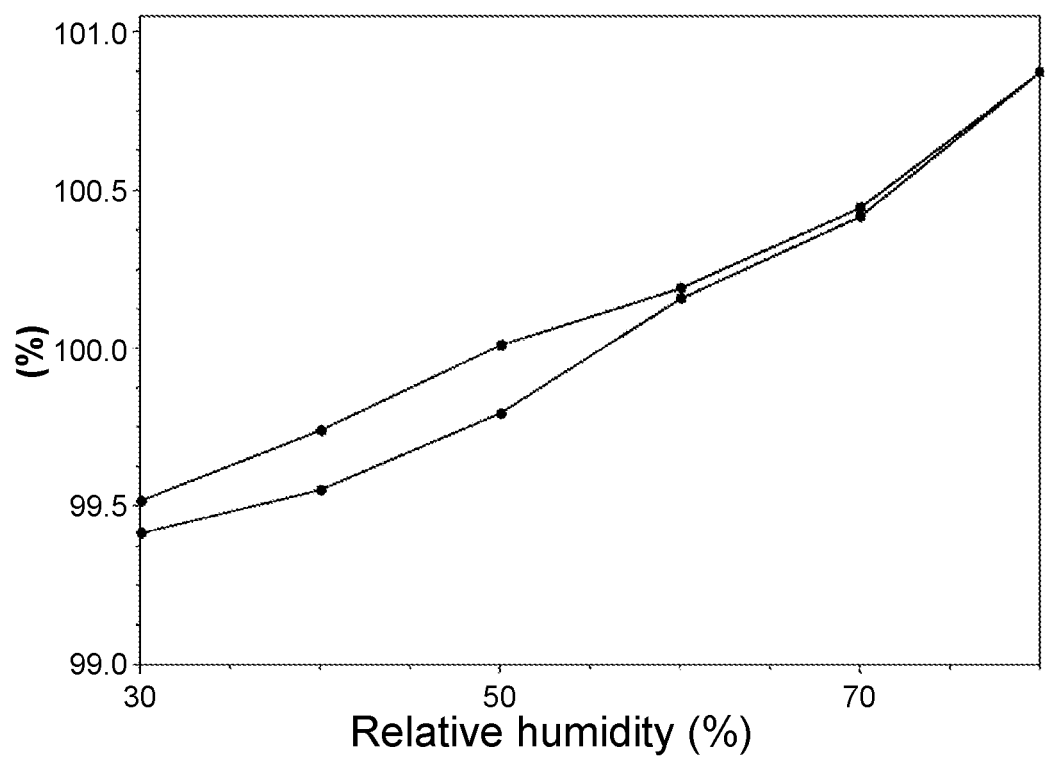
FIG. 9 is the isothermal sorption plot of ACP-196 malate Form 1 prepared by the present invention.

Its isothermal sorption plot is shown in FIG. 9, showing a weight change of about 1.5% in the range of 30% to 80% relative humidity.

Example 2

Placed 200 mg ACP-196 of Preparation Example 1 in 4 mL isopropanol to form a solution, slowly and dropwisely added 3 mL isopropanol solution containing malic acid (0.8 eq), stirred for 1 day for crystallization and precipitation, filtrated, and then vacuum dried at room temperature for 20 hours to obtain 170 mg ACP-196 malate Form 1; 82% yield.

Example 3

Placed 200 mg ACP-196 of Preparation Example 1 in 2 mL acetone to form a solution, slowly and dropwisely added 1 mL acetone solution containing malic acid (1 eq), stirred for 1 day for crystallization and precipitation, filtrated, and then vacuum dried at room temperature for 10 hours to obtain 150 mg ACP-196 malate Form 1; 58% yield.

Example 4

ACP-196 malate Form 1 can also be obtained by replacing the solvents in Example 3 with solvents in the following table.

| Experiment Number | Solvent 1 (ACP-196) | Solvent 2 (malic acid) |
|---|---|---|
| Experiment 1 | Ethanol | Ethanol |
| Experiment 2 | n-Propanol | n-Propanol |
| Experiment 3 | sec-Butanol | sec-Butanol |
| Experiment 4 | Acetone | Methanol |
| Experiment 5 | Butanone | Acetone |
| Experiment 6 | Isopropanol | Acetone |
| Experiment 7 | n-Propanol | Ethanol |
| Experiment 8 | Acetone | Butanone |
| Experiment 9 | Acetone | Isopropanol |

Example 5

Placed 30 mg ACP-196 of Preparation Example 1 and 6.9 mg malic acid in 1.5 mL tetrahydrofuran to form a solution, added 5 mL isopropyl ether, stirred for 1 day for crystallization and precipitation, filtrated, and then vacuum dried at room temperature for 24 hours to obtain 26 mg ACP-196 malate Form 1; 84% yield.

Example 6

Placed 50 mg ACP-196 of Preparation Example 1 and 15.8 mg malic acid in 1 mL tetrahydrofuran to form a solution, added 4 mL isopropyl ether, stirred for 3 days for crystallization and precipitation, filtrated, and then vacuum dried at room temperature for 48 hours to obtain 53 mg ACP-196 malate Form 1; 82% yield.

Example 7

Placed 40 mg ACP-196 of Preparation Example 1 and 11.5 mg malic acid in 0.4 mL dichloromethane to form a solution, added 2.5 mL n-heptane, stirred for 2 days for crystallization and precipitation, filtrated, and then vacuum dried at room temperature for 30 hours to obtain 37 mg ACP-196 malate Form 1; 72% yield.

Example 8

ACP-196 malate Form 1 can also be obtained by replacing the solvents in Example 7 with the following table.

| Experiment Number | Co-solvent | Anti-solvent |
|---|---|---|
| Experiment 1 | Ethyl acetate | Methylcyclohexane |
| Experiment 2 | Isopropyl acetate | Toluene |
| Experiment 3 | 1,4-Dioxane | Methyl tert-butyl ether |
| Experiment 4 | Acetonitrile | Diethyl ether |
| Experiment 5 | Chloroform | Cyclohexane |
| Experiment 6 | Dichloromethane | Isopropyl ether |
| Experiment 7 | Tetrahydrofuran | n-Hexane |

$^1$H-NMR data, XRPD patterns, PLM plots, TGA thermograms, DSC thermograms, isothermal sorption plots (not shown) of the samples prepared in Examples 2 to 8 are the same as or similar to that of the sample prepared in Example 1, indicating the crystalline forms obtained in Examples 2 to 8 are the same as that of Example 1.

Example 9

Placed 3 g ACP-196 of Preparation Example 1 in 75 mL acetone to form a solution, slowly and dropwisely added 60 mL acetone solution containing fumaric acid (1.1 eq), stirred for 2 days for crystallization and precipitation, filtrated, and then vacuum dried at room temperature for 24 hours to obtain 3 g ACP-196 hemifumarate Form 1; 89% yield. $^1$H-NMR (d6-DMSO, 500 MHz): 10.84 (s, 1H), 8.50-8.34 (m, 1H), 8.32-8.08 (m, 2H), 7.87 (td, 3H), 7.26-7.04 (m, 2H), 6.22 (s, 2H), 5.73 (dd, 1H), 5.49 (dd, 1H), 4.26 (s, 1H), 3.84 (t, 1H), 3.62 (dtt, 1H), 2.62 (dd, 1H), 2.48-2.18 (m, 3H), 2.15 (dt, 1H), 2.08-1.92 (m, 2H), 1.64 (s, 1H).

The results shows that ACP-196 and fumaric acid formed a salt at a molar ratio of about 2:1.

Figure 10:
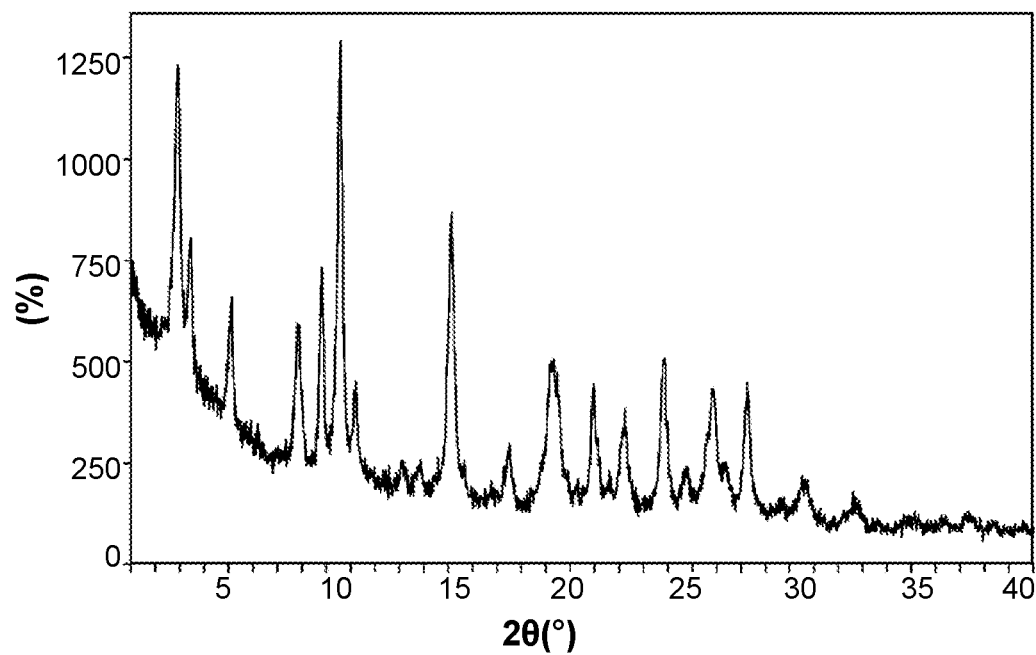
FIG. 10 is the XRPD pattern of ACP-196 hemifumarate Form 1 prepared by the present invention.

Its XRPD pattern is shown in FIG. 10, showing as crystalline.

Figure 11:
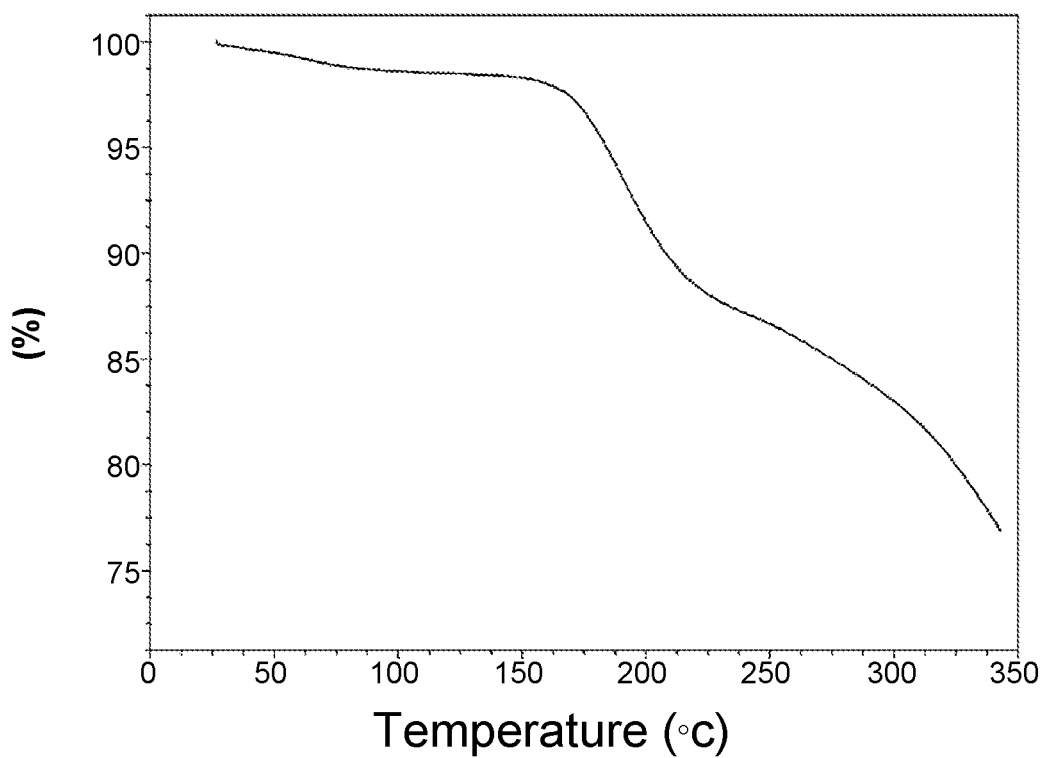
FIG. 11 is the TGA thermogram of ACP-196 hemifumarate Form 1 prepared by the present invention.

Its TGA thermogram is shown in FIG. 11, showing an anhydrate with a decomposition temperature at about 170° C.

Figure 12:
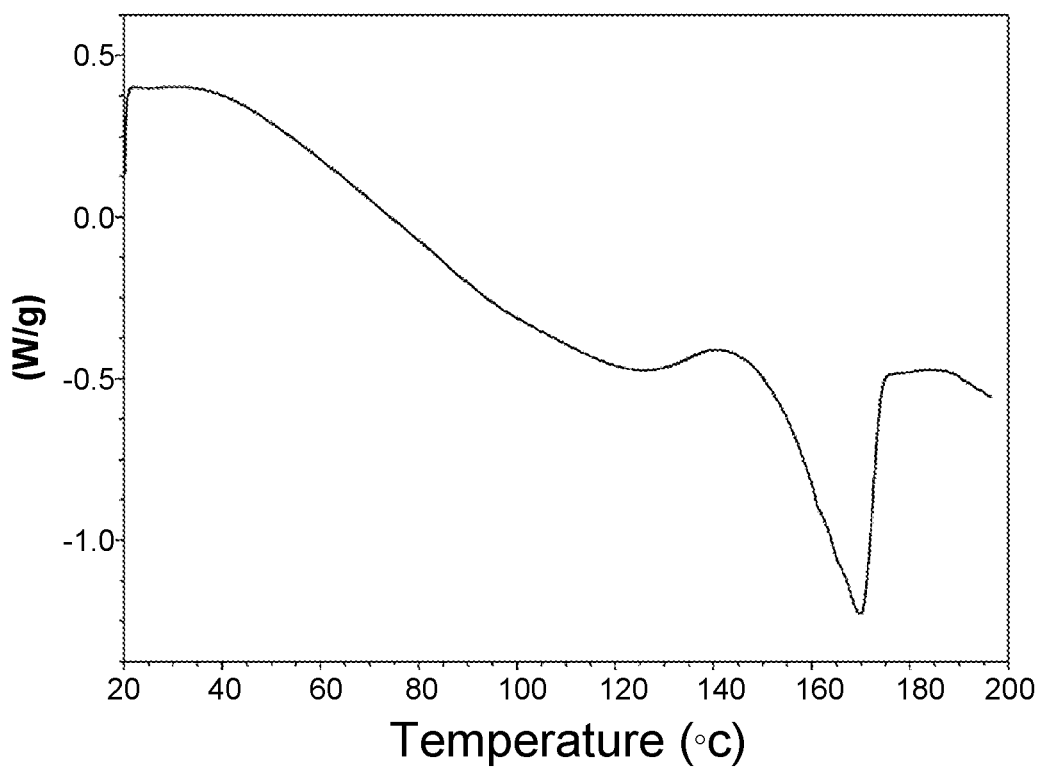
FIG. 12 is the DSC thermogram of ACP-196 hemifumarate Form 1 prepared by the present invention.

Its DSC thermogram is shown in FIG. 12, showing an melting point at about 153° C.

Figure 13:
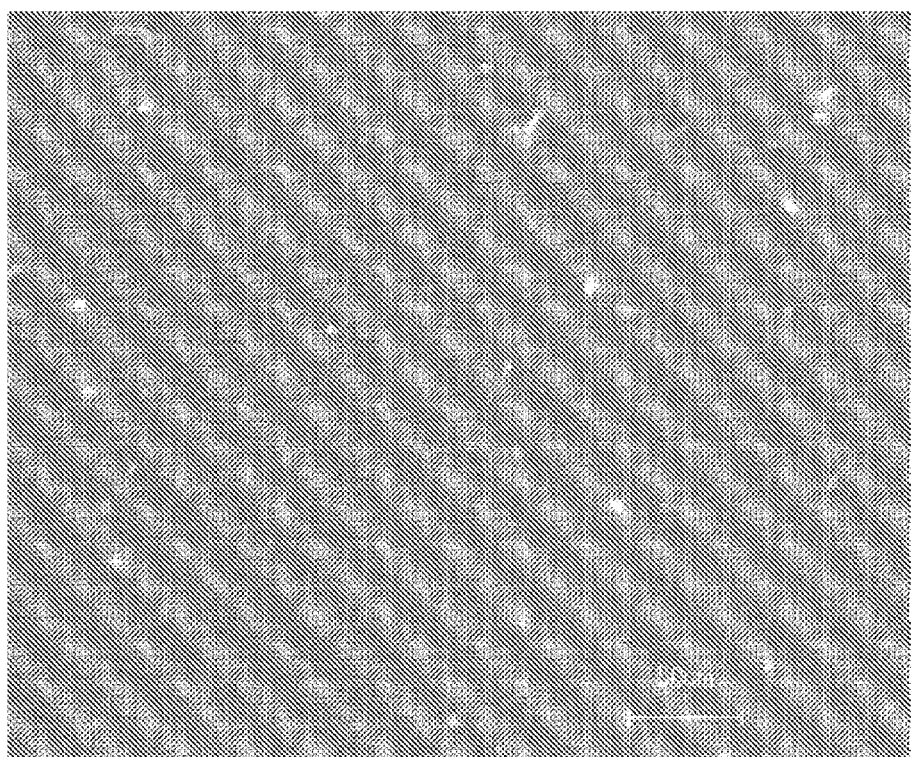
FIG. 13 is the PLM plot of ACP-196 hemifumarate Form 1 prepared by the present invention.

Its PLM plot is shown in FIG. 13, showing granular fine particles.

Figure 14:
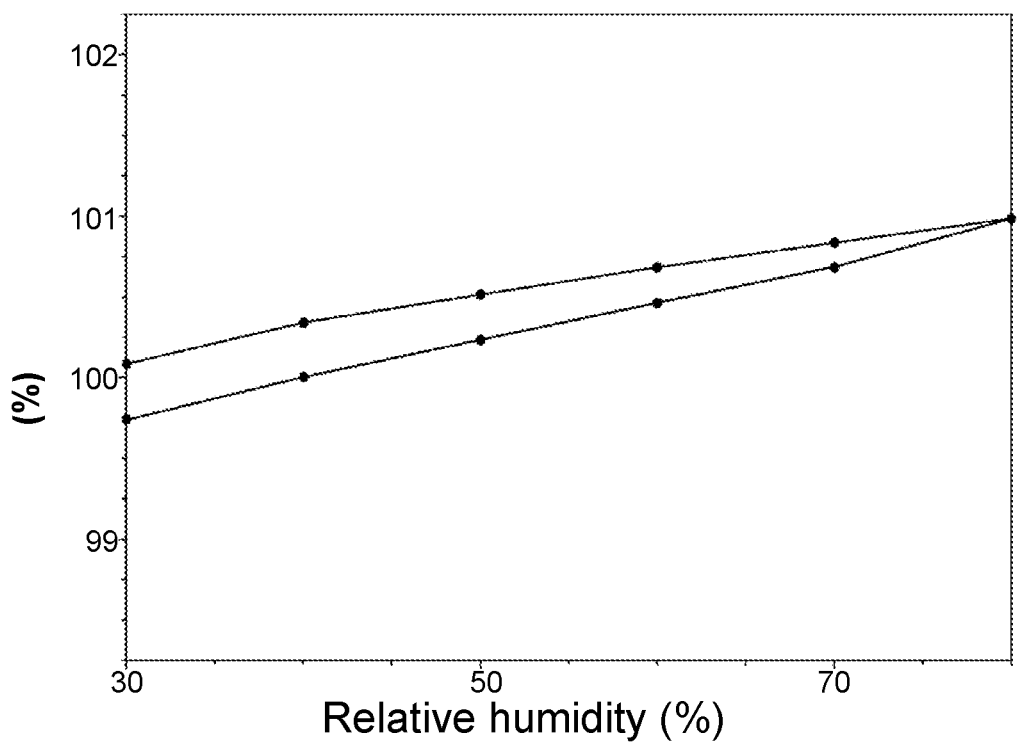
FIG. 14 is the isothermal sorption plot of ACP-196 hemifumarate Form 1 prepared by the present invention.

Its isothermal sorption plot is shown in FIG. 14, showing a weight change of about 1.2% in the range of 30% to 80% relative humidity.

Example 10

Placed 200 mg ACP-196 of Preparation Example 1 in 2 mL acetone to form a solution, slowly and dropwisely added 3 mL acetone solution containing fumaric acid (0.5 eq), stirred for 1 day for crystallization and precipitation, filtrated, and then vacuum dried at room temperature for 10 hours to obtain 183 mg ACP-196 hemifumarate Form 1; 81% yield.

Example 11

Placed 200 mg ACP-196 of Preparation Example 1 in 1 mL methanol to form a solution, slowly and dropwisely added 6 mL methanol solution containing fumaric acid (0.8 eq), stirred for 1 day for crystallization and precipitation, filtrated, and then vacuum dried at room temperature for 24 hours to obtain 165 mg ACP-196 hemifumarate Form 1; 73% yield.

Example 12

ACP-196 hemifumarate Form 1 can also be obtained by replacing the solvents in Example 11 with the following table.

| Experiment Number | Solvent 1 (ACP-196) | Solvent 2 (fumaric acid) |
|---|---|---|
| Experiment 1 | Acetone | Isopropanol |
| Experiment 2 | Acetone | Ethanol |
| Experiment 3 | Butanone | Methanol |
| Experiment 4 | Butanone | sec-Butanol |
| Experiment 5 | Methanol | Acetone |
| Experiment 6 | Ethanol | Butanone |

Example 13

Placed 200 mg ACP-196 of Preparation Example 1 and 24.9 mg fumaric acid in 4 mL 1,4-dioxane to form a solution, added 6 mL isopropyl ether, stirred for 1 day for crystallization and precipitation, filtrated, and then vacuum dried at room temperature for 24 hours to obtain 198 mg ACP-196 hemifumarate Form 1; 88% yield.

Example 14

Placed 300 mg ACP-196 of Preparation Example 1 and 82.3 mg fumaric acid in 3 mL 1,4-dioxane to form a solution, added 5 mL isopropyl ether, stirred for 3 days for crystallization and precipitation, filtrated, and then vacuum dried at room temperature for 48 hours to obtain 287 mg ACP-196 hemifumarate Form 1; 85% yield.

Example 15

Placed 40 mg ACP-196 of Preparation Example 1 and 8.0 mg fumaric acid in 2 mL tetrahydrofuran to form a solution, added 6 mL isopropyl ether, stirred for 2 days for crystallization and precipitation, filtrated, and then vacuum dried at room temperature for 30 hours to obtain 36 mg ACP-196 hemifumarate Form 1; 80% yield.

Example 16

ACP-196 hemifumarate Form 1 can also be obtained by replacing the solvents in Example 15 with the following table.

| Experiment Number | Co-solvent | Anti-solvent |
|---|---|---|
| Experiment 1 | Ethyl acetate | Methyl tert-butyl ether |
| Experiment 2 | Isopropyl acetate | Diethyl ether |
| Experiment 3 | Tetrahydrofuran | n-Heptane |
| Experiment 4 | 1,4-Dioxane | n-Hexane |
| Experiment 5 | Acetonitrile | Toluene |
| Experiment 6 | Dichloromethane | Toluene |
| Experiment 7 | Chloroform | Isopropyl ether |
| Experiment 8 | Chloroform | Methylcyclohexane |

$^1$H-NMR data, XRPD patterns, PLM plots, TGA thermograms, DSC thermograms, isothermal sorption plots (not shown) of the samples prepared in Examples 10 to 16 are the same as or similar to that of the sample prepared in Example 9, indicating the crystalline forms obtained in Examples 10 to 16 are the same as that of Example 1.

Example 17

Placed 3 g ACP-196 of Preparation Example 1 in 100 mL isopropanol to form a solution, slowly added 50 mL isopropanol solution containing maleic acid (1.1 eq), stirred for 2 days for crystallization and precipitation, filtrated, and then vacuum dried at room temperature for 24 hours to obtain 3.15 g ACP-196 maleate Form 1; 84% yield. $^1$H NMR (d6-DMSO, 500 MHz): 10.88 (d, 1H), 8.42 (d, 1H), 8.22 (dd, 2H), 8.11-7.69 (m, 3H), 7.64-6.88 (m, 3H), 6.16 (s, 2H), 5.77 (dd, 1H), 5.52 (dd, 1H), 3.94-3.54 (m, 3H), 2.45-1.89 (m, 5H), 1.69 (s, 1H), 1.05 (d, 1H). The results shows that ACP-196 and maleic acid formed a salt at a molar ratio of about 1:1.

Figure 15:
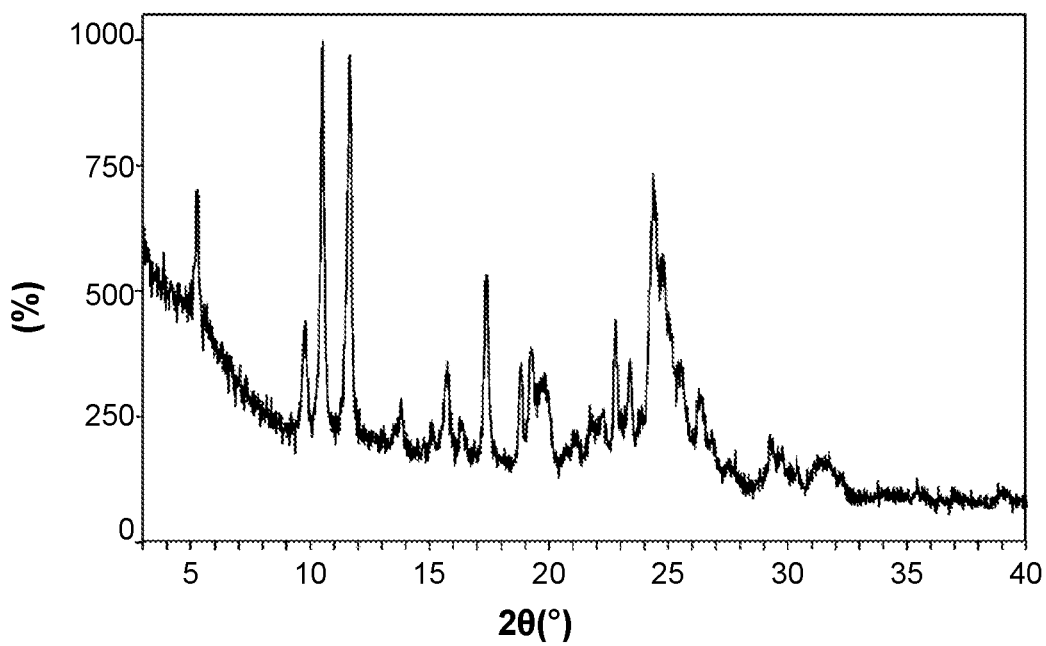
FIG. 15 is the XRPD pattern of ACP-196 maleate Form 1 prepared by the present invention.

Its XPRD pattern is shown in FIG. 15, showing it is crystalline.

Figure 16:
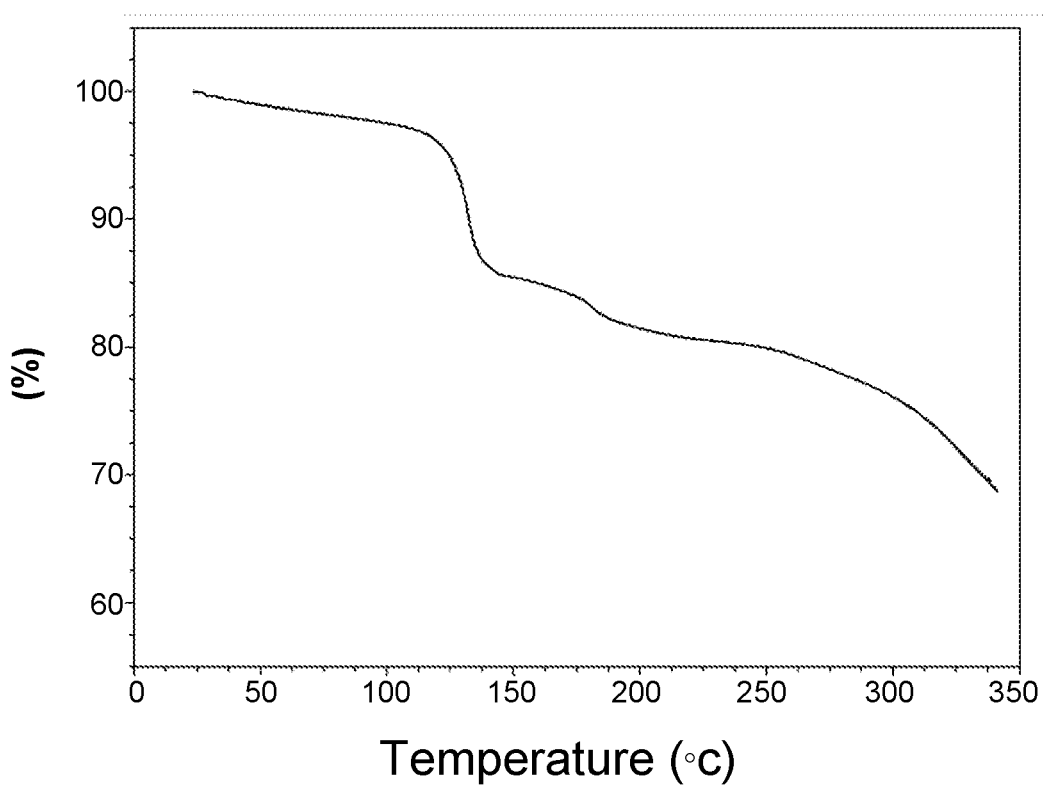
FIG. 16 is the TGA thermogram of ACP-196 maleate Form 1 prepared by the present invention.

Its TGA thermogram is shown in FIG. 16, showing an anhydrate with a decomposition temperature at about 125° C.

Figure 17:
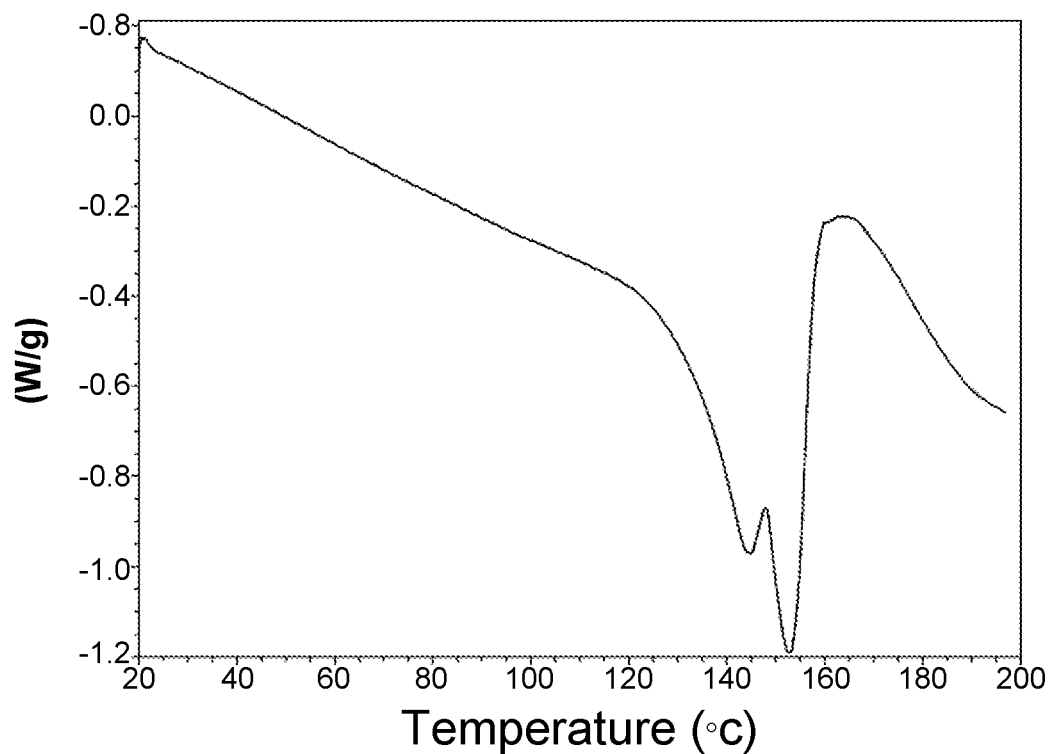
FIG. 17 is the DSC thermogram of ACP-196 maleate Form 1 prepared by the present invention.

Its DSC thermogram is shown in FIG. 17, showing an melting point at about 132° C.

Figure 18:
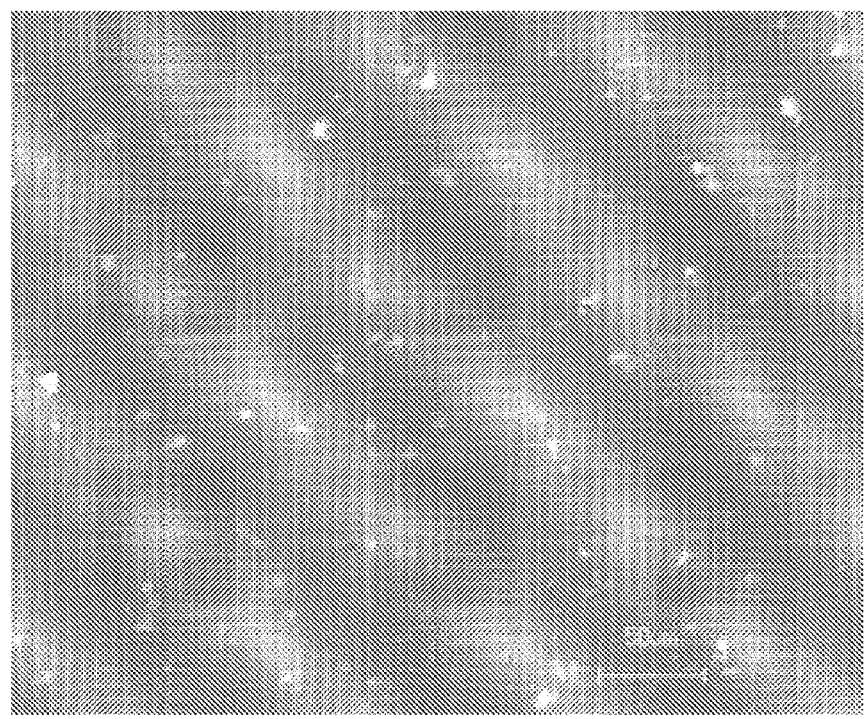
FIG. 18 is the PLM plot of ACP-196 maleate Form 1 prepared by the present invention.

Its PLM plot is shown in FIG. 18, showing granular fine particles.

Figure 19:
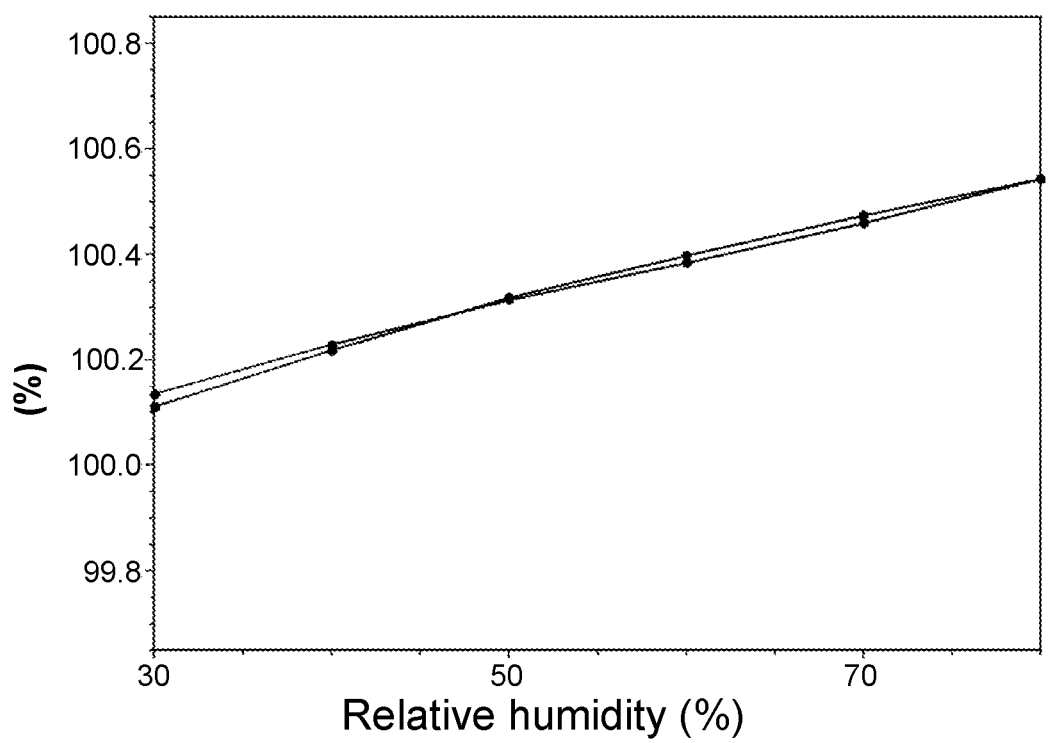
FIG. 19 is the isothermal sorption plot of ACP-196 maleate Form 1 prepared by the present invention.

Its isothermal sorption plot is shown in FIG. 19, showing a weight change of about 0.4% in the range of 30% to 80% relative humidity.

Example 18

Placed 100 mg ACP-196 of Preparation Example 1 in 2 mL isopropanol to form a solution, slowly and dropwisely added 2 mL isopropanol solution containing maleic acid (0.8 eq), stirred for 1 day for crystallization and precipitation, filtrated, and then vacuum dried at room temperature for 18 hours to obtain 79 mg ACP-196 maleate Form 1; 79% yield.

Example 19

Placed 100 mg ACP-196 of Preparation Example 1 in 1 mL acetone to form a solution, slowly and dropwisely added 1 mL acetone solution containing maleic acid (1.0 eq), stirred for 1 day for crystallization and precipitation, filtrated, and then vacuum dried at room temperature for 48 hours to obtain 95 mg ACP-196 maleate Form 1; 76% yield.

Example 20

ACP-196 maleate Form 1 can also be obtained by replacing the solvents in Example 19 with the following table.

| Experiment Number | Solvent 1 (ACP-196) | Solvent 2 (maleic acid) |
|---|---|---|
| Experiment 1 | Isopropanol | Ethanol |
| Experiment 2 | sec-Butanol | sec-Butanol |
| Experiment 3 | Ethanol | Acetone |
| Experiment 4 | Acetone | Butanone |
| Experiment 5 | Butanone | Methanol |
| Experiment 6 | Acetone | Ethanol |

Example 21

Placed 30 mg ACP-196 of Preparation Example 1 and 6.0 mg maleic acid in 1.5 mL tetrahydrofuran to form a solution, added 6 mL n-heptane, stirred for 1 day for crystallization and precipitation, filtrated, and then vacuum dried at room temperature for 24 hours to obtain 25 mg ACP-196 malate Form 1; 83% yield.

Example 22

Placed 50 mg ACP-196 of Preparation Example 1 and 13.7 mg maleic acid in 1 mL tetrahydrofuran to form a solution, added 5 mL n-heptane, stirred for 3 days for crystallization and precipitation, filtrated, and then vacuum dried at room temperature for 48 hours to obtain 49 mg ACP-196 malate Form 1; 78% yield.

Example 23

Placed 100 mg ACP-196 of Preparation Example 1 and 24.9 mg maleic acid in 1 mL dichloromethane to form a solution, added 5 mL n-heptane, stirred for 2 days for crystallization and precipitation, filtrated, and then vacuum dried at room temperature for 30 hours to obtain 96 mg ACP-196 malate Form 1; 77% yield.

Example 24

ACP-196 malate Form 1 can also be obtained by replacing the solvents in Example 23 with the following table.

| Experiment Number | Co-solvent | Anti-solvent |
| --- | --- | --- |
| Experiment 1 | Chloroform | Isopropyl ether |
| Experiment 2 | Dichloromethane | Methyl tert-butyl ether |
| Experiment 3 | Acetonitrile | Diethyl ether |
| Experiment 4 | 1,4-Dioxane | Diethyl ether |
| Experiment 5 | Tetrahydrofuran | n-Hexane |
| Experiment 6 | Isopropyl acetate | Methylcyclohexane |
| Experiment 7 | Ethyl acetate | Toluene |
| Experiment 8 | Ethyl acetate | n-Heptane |

$^1$H-NMR data, XRPD patterns, PLM plots, TGA thermograms, DSC thermograms, isothermal sorption plots (not shown) of the samples prepared in Examples 18 to 24 are the same as or similar to that of the sample prepared in Example 17, indicating the crystalline forms obtained in Examples 18 to 24 are the same as that of Example 17.

Example 25

Placed 3 g ACP-196 of Preparation Example 1 in 100 mL isopropanol to form a solution, slowly added 20 mL isopropanol solution containing phosphoric acid (1.1 eq), stirred for 2 days for crystallization and precipitation, filtrated, and then vacuum dried at room temperature for 24 hours to obtain 285 mg ACP-196 phosphate Form 1; 75% yield.

The IC analysis shows that the PO43-content in ACP-196 phosphate Form 1 is 20.1%, the theoretical PO43-content in monophosphate is 16.9%, and the theoretical PO43-content in diphosphate is 28.7%. Therefore, the molar ratio of ACP-196 to phosphoric acid is about 1:1.

Figure 20:
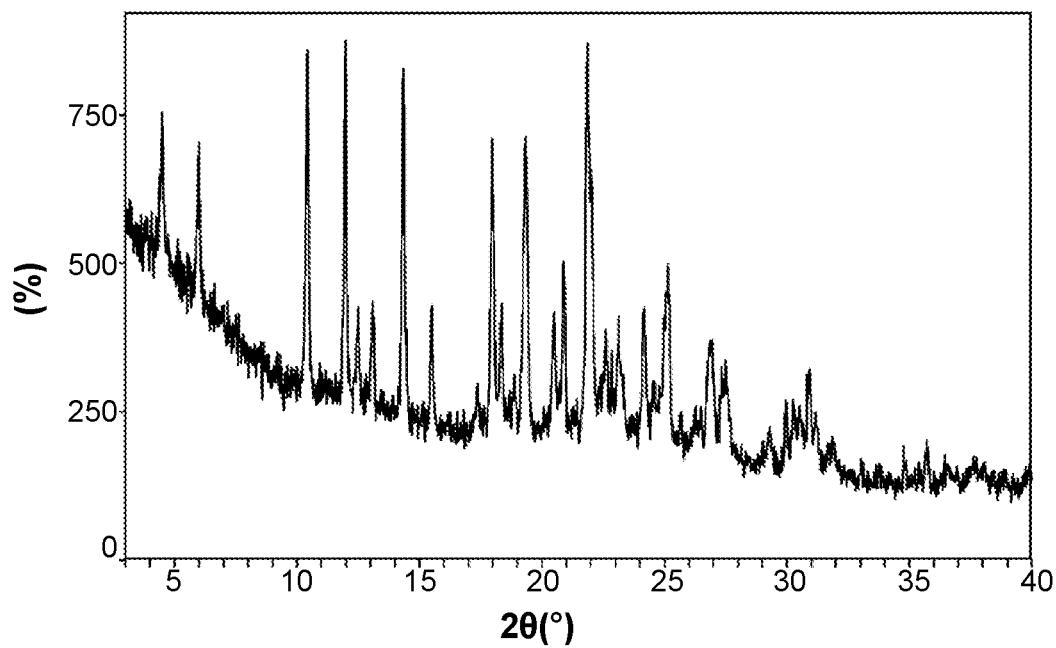
FIG. 20 is the XRPD pattern of ACP-196 phosphate Form 1 prepared by the present invention.

Its XRPD pattern is shown in FIG. 20, showing it is crystalline.

Figure 21:
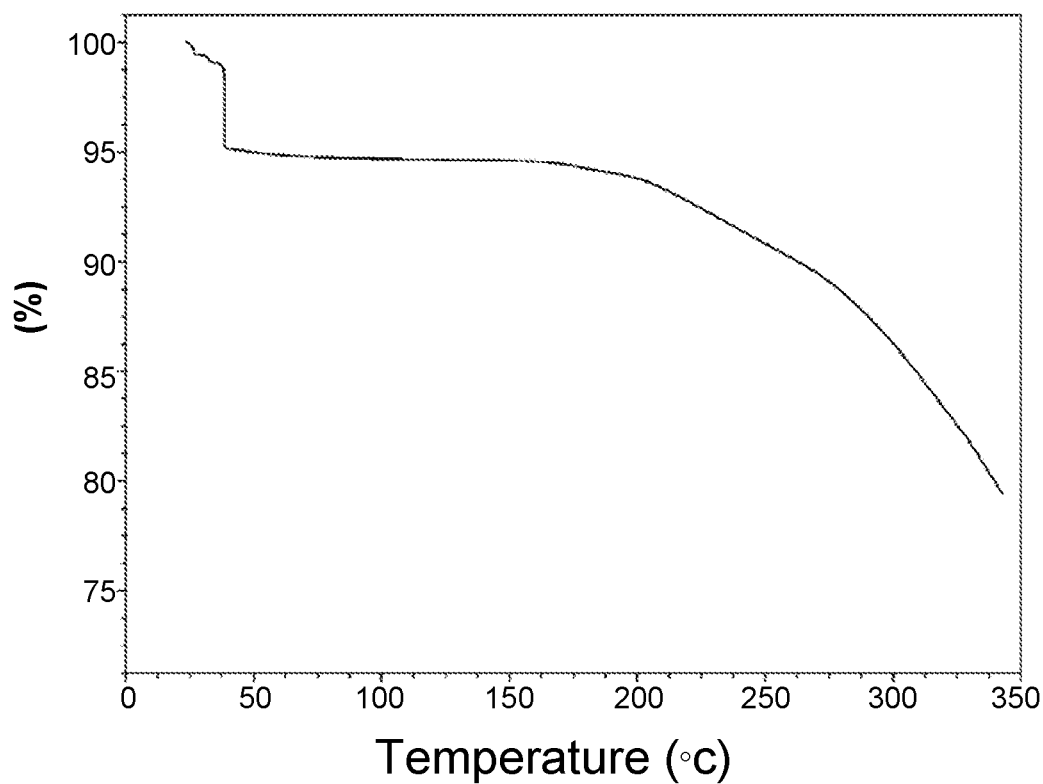
FIG. 21 is the TGA thermogram of ACP-196 phosphate Form 1 prepared by the present invention.

Its TGA thermogram is shown in FIG. 21, combined with a 4.3% stepwise weight loss shown as a sesquihydrate, and a decomposition temperature at about 198° C.

Figure 22:
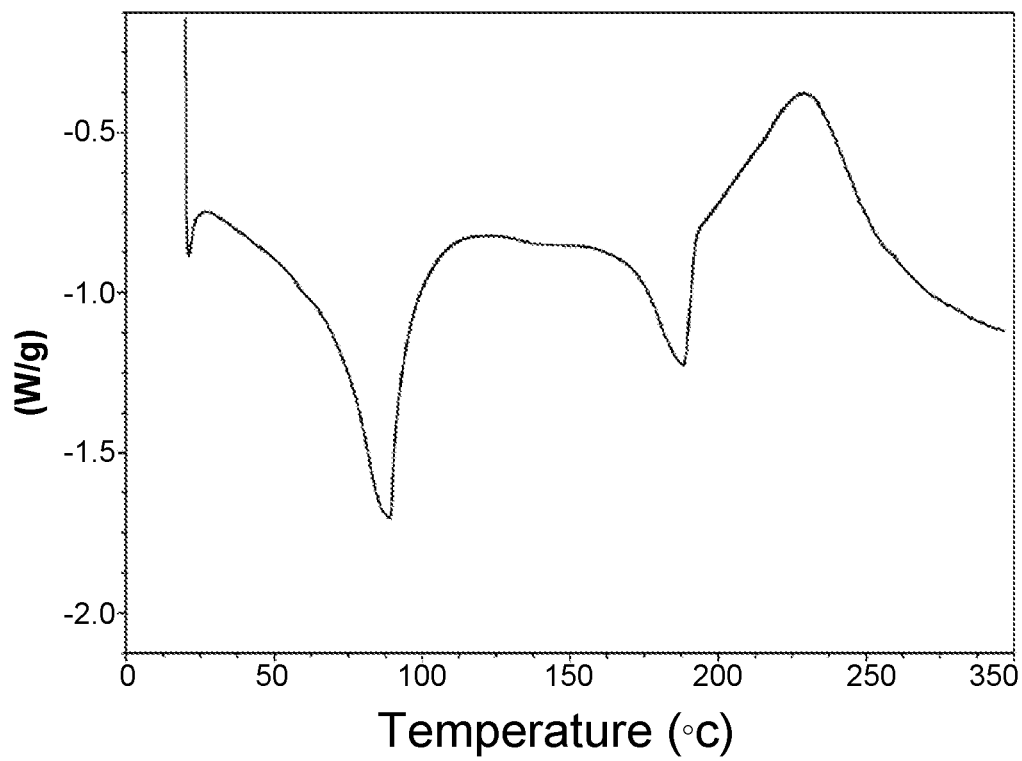
FIG. 22 is the DSC thermogram of ACP-196 phosphate Form 1 prepared by the present invention.

Its DSC thermogram is shown in FIG. 22, showing an melting point at about 170° C.

Figure 23:
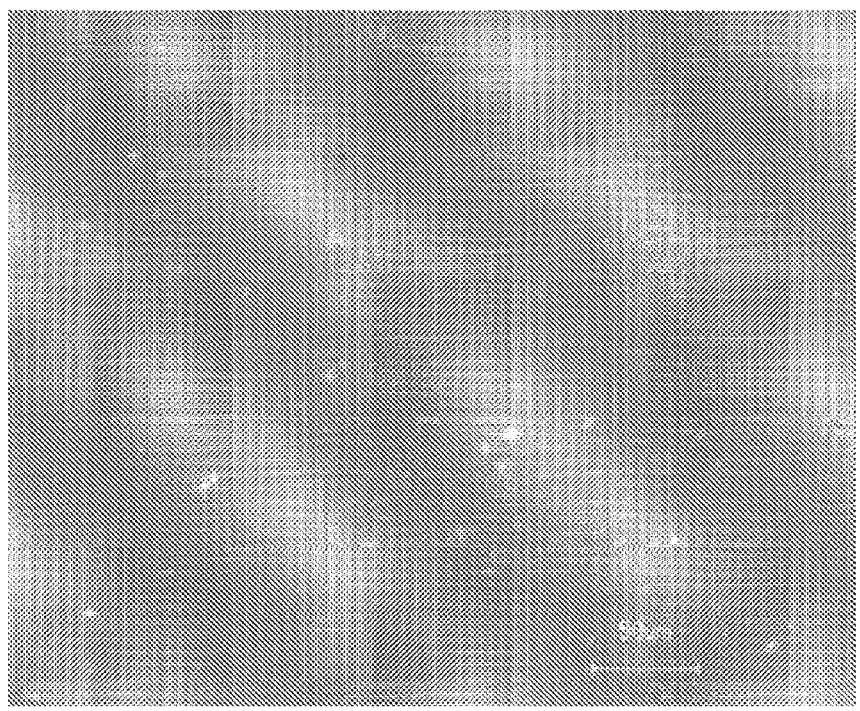
FIG. 23 is the PLM plot of ACP-196 phosphate Form 1 prepared by the present invention.

Its PLM plot is shown in FIG. 23, showing granular block particles.

Figure 24:
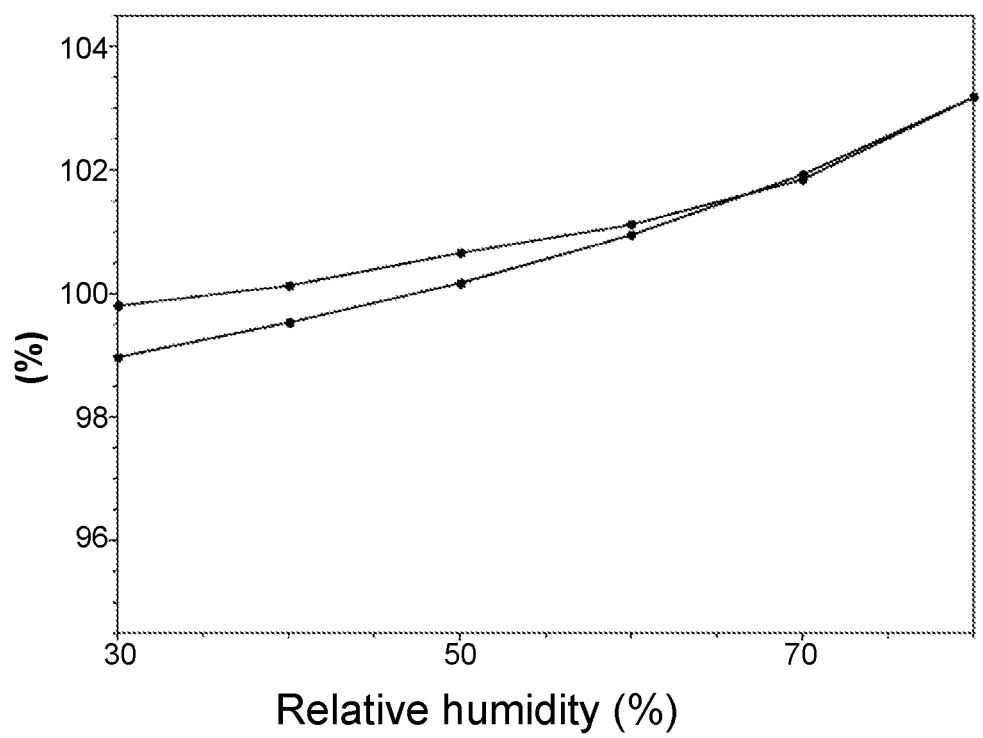
FIG. 24 is the isothermal sorption plot of ACP-196 phosphate Form 1 prepared by the present invention.

Its isothermal sorption plot is shown in FIG. 24, showing a weight change of about 4.2% in the range of 30% to 80% relative humidity.

Example 26

Placed 100 mg ACP-196 of Preparation Example 1 in 2 mL isopropanol to form a solution, slowly and dropwisely added 1 mL isopropanol solution containing phosphoric acid (0.8 eq), stirred for 1 day for crystallization and precipitation, filtrated, and then vacuum dried at room temperature for 40 hours to obtain 70 mg ACP-196 phosphate Form 1; 69% yield.

Example 27

Placed 100 mg ACP-196 of Preparation Example 1 in 1 mL acetone to form a solution, slowly added 1 mL acetone solution containing phosphoric acid (1.0 eq), stirred for 1 day for crystallization and precipitation, filtrated, and then vacuum dried at room temperature for 36 hours to obtain 80 mg ACP-196 phosphate Form 1; 63% yield.

Example 28

ACP-196 phosphate Form 1 can also be obtained by replacing the solvents in Example 27 with the following table.

| Experiment Number | Solvent 1 (ACP-196) | Solvent 2 (malic acid) |
| --- | --- | --- |
| Experiment 1 | Methanol | Ethanol |
| Experiment 2 | n-Propanol | Methanol |
| Experiment 3 | sec-Butanol | sec-Butanol |
| Experiment 4 | n-Butanol | Butanone |
| Experiment 5 | Butanone | Butanone |
| Experiment 6 | Acetone | Isopropanol |

Example 29

Placed 100 mg ACP-196 of Preparation Example 1 in 2 mL dichloroform to form a solution, dropwisely added 19.8 mg 85% phosphoric acid, then added 5 mL methylcyclohexane, stirred for 1 day for crystallization and precipitation, filtrated, and then vacuum dried at room temperature for 24 hours to obtain 87 mg ACP-196 phosphate Form 1; 86% yield.

Example 30

Placed 100 mg ACP-196 of Preparation Example 1 in 1 mL dichloroform to form a solution, added 27.2 mg 85% phosphoric acid, then added 2.5 mL methylcyclohexane, stirred for 3 days for crystallization and precipitation, filtrated, and then vacuum dried at room temperature for 30 hours to obtain 105 mg ACP-196 phosphate Form 1; 83% yield.

Example 31

Placed 300 mg ACP-196 of Preparation Example 1 in 2 mL chloroform to form a solution, dropwisely added 66.9 mg 85% phosphoric acid, then added 6 mL n-heptane, stirred for 3 days for crystallization and precipitation, filtrated, and then vacuum dried at room temperature for 36 hours to obtain 276 mg ACP-196 phosphate Form 1; 81% yield.

Example 32

ACP-196 phosphate Form 1 can also be obtained by replacing the solvents in Example 31 with the following table.

| Experiment Number | Co-solvent | Anti-solvent |
|---|---|---|
| Experiment 1 | Ethyl acetate | Isopropyl ether |
| Experiment 2 | Isopropyl acetate | n-Heptane |
| Experiment 3 | Tetrahydrofuran | Methyl tert-butyl ether |
| Experiment 4 | 1,4-Dioxane | Diethyl ether |
| Experiment 5 | Acetonitrile | Methylcyclohexane |
| Experiment 6 | Dichloromethane | n-Hexane |
| Experiment 7 | Chloroform | Diethyl ether |
| Experiment 8 | Tetrahydrofuran | Toluene |

IC data, XRPD patterns, PLM plots, TGA thermograms, DSC thermograms, isothermal sorption plots (not shown) of the samples prepared in Examples 26 to 32 are the same as or similar to that of the sample prepared in Example 25, indicating the crystalline forms obtained in Examples 26 to 32 are the same as that of Example 25.

Example 33

Placed 3 g ACP-196 of Preparation Example 1 in 100 mL isopropanol to form a solution, slowly added 20 mL isopropanol solution containing sulfuric acid (1.1 eq), stirred for 2 days for crystallization and precipitation, filtrated, and then vacuum dried at room temperature for 16 hours to obtain 2.8 g ACP-196 sulfate Form 1; 77% yield.

The IC analysis shows that the SO42-content in ACP-196 sulfate Form 1 is 18.2%, the theoretical SO42-content in monosulfate is 17.0%, and the theoretical SO42-content in disulfate is 29.0%. Therefore, the molar ratio of ACP-196 to phosphoric acid is about 1:1.

Figure 25:
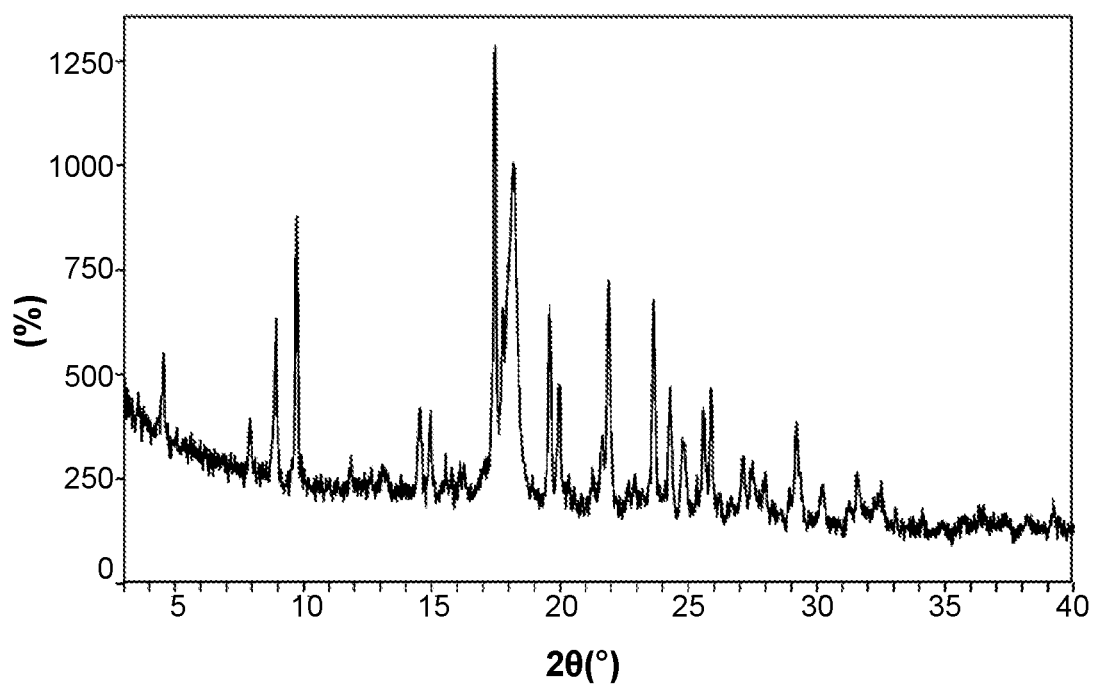
FIG. 25 is the isothermal sorption plot of ACP-196 sulfate Form 1 prepared by the present invention.

Its XRPD pattern is shown in FIG. 25.

Example 34

Placed 300 mg ACP-196 of Preparation Example 1 in 6 mL isopropanol to form a solution, slowly and dropwisely added 2 mL acetone solution containing sulfuric acid (0.8 eq), stirred for 1 day for crystallization and precipitation, filtrated, and then vacuum dried at room temperature for 20 hours to obtain 220 mg ACP-196 sulfate Form 1; 76% yield.

Example 35

Placed 300 mg ACP-196 of Preparation Example 1 in 3 mL acetone to form a solution, slowly added 1 mL acetone solution containing sulfuric acid (1.0 eq), stirred for 1 day for crystallization and precipitation, filtrated, and then vacuum dried at room temperature for 20 hours to obtain 250 mg ACP-196 sulfate Form 1; 69% yield.

Example 36

ACP-196 sulfate Form 1 can also be obtained by replacing the solvents in Example 35 with the following table.

| Experiment Number | Solvent 1 (ACP-196) | Solvent 2 (sulfuric acid) |
|---|---|---|
| Experiment 1 | Methanol | Methanol |
| Experiment 2 | Ethanol | Acetone |
| Experiment 3 | sec-Butanol | Ethanol |
| Experiment 4 | n-Butanol | Isopropanol |
| Experiment 5 | Butanone | Butanone |
| Experiment 6 | Acetone | n-Propanol |

Example 37

Placed 50 mg ACP-196 of Preparation Example 1 in 2 mL ethyl acetate to form a solution, dropwisely added 8.6 mg concentrated sulfuric acid, then added 3 mL n-hexane, stirred for 1 day for crystallization and precipitation, filtrated, and then vacuum dried at room temperature for 24 hours to obtain 40 mg ACP-196 sulfate Form 1; 81% yield.

Example 38

Placed 200 mg ACP-196 of Preparation Example 1 in 4 mL ethyl acetate to form a solution, added 47.3 mg concentrated sulfuric acid, then added 6 mL n-hexane, stirred for 3 days for crystallization and precipitation, filtrated, and then vacuum dried at room temperature for 48 hours to obtain 192 mg ACP-196 sulfate Form 1; 79% yield.

Example 39

Placed 300 mg ACP-196 of Preparation Example 1 in 30 mL tetrahydrofuran to form a solution, dropwisely added 58.0 mg concentrated sulfuric acid, then added 30 mL diethyl ether, stirred for 2 days for crystallization and precipitation, filtrated, and then vacuum dried at room temperature for 20 hours to obtain 210 mg ACP-196 sulfate Form 1; 63% yield.

Example 40

ACP-196 sulfate Form 1 can also be obtained by replacing the solvents in Example 39 with the following table.

| Experiment Number | Co-solvent | Anti-solvent |
|---|---|---|
| Experiment 1 | Tetrahydrofuran | Toluene |
| Experiment 2 | 1,4-Dioxane | Isopropyl ether |
| Experiment 3 | Acetonitrile | Diethyl ether |
| Experiment 4 | Ethyl acetate | Methyl tert-butyl ether |
| Experiment 5 | Isopropyl acetate | n-Heptane |
| Experiment 6 | Dichloromethane | Methylcyclohexane |
| Experiment 7 | Chloroform | n-Hexane |
| Experiment 8 | Chloroform | Methyl tert-butyl ether |

IC data, XRPD patterns (not shown) of the samples prepared in Examples 34 to 40 are the same as or similar to that of the sample prepared in Example 33, indicating the crystalline forms obtained in Examples 34 to 40 are the same as that of Example 33.

Example 41

| Component (active ingredient basis) | Dosage (mg) |
|---|---|
| ACP-196 malate Form 1/ACP-196 hemifumarate Form 1/ACP-196 maleate Form 1/ACP-19 phosphate Form 1/ACP-196 sulfate Form 1 | 50 |

| Component (active ingredient basis) | Dosage (mg) |
|---|---|
| Compressible starch | 110 |
| Cross-linked providone | 5 |
| Microcrystalline cellulose | 80 |
| Silica | 5 |
| Total | 250 |

Mixed ACP-196 malate Form 1 or ACP-196 hemifumarate Form 1 or ACP-196 maleate Form 1 or ACP-196 phosphate Form 1 or ACP-196 sulfate Form 1, compressible starch, microcrystalline cellulose and crosslinked polyvinyl ketone, then use silica as lubricant, and then finally compressed as tablets.

Example 42

| Component (active ingredient basis) | Dosage (mg) |
|---|---|
| ACP-196 malate Form 1/ACP-196 hemifumarate Form 1/ACP-196 maleate Form 1/ACP-196 phosphate Form 1/ACP-196 sulfate Form 1 | 100 |
| Ethyl cellulose | 100 |
| Hydroxypropylmethylcellulose | 10 |
| Lactose | 110 |
| Microcrystalline cellulose | 80 |
| Magnesium stearate | 5 |
| Talc | 5 |
| Total | 410 |

Mixed ACP-196 malate Form 1 or ACP-196 hemifumarate Form 1 or ACP-196 maleate Form 1 or ACP-196 phosphate Form 1 or ACP-196 sulfate Form 1, ethyl cellulose, hydroxypropyl methyl cellulose, lactose and microcrystalline cellulose, granulated with 75% ethanol, dried, crushed, shifted through 80 mesh sieve, then added magnesium stearate and talc to mix evenly and filled into the capsule.

Comparative Example 1

Solubility test: took 20 mg ACP-196 of Preparation Example 1, 20 mg ACP-196 malate Form 1 of the invention, 20 mg ACP-196 hemifumarate Form 1 of the invention, 20 mg ACP-196 maleate Form 1 of the invention, 20 mg ACP-196 phosphate Form 1 of the invention and 20 mg ACP-196 sulfate Form 1 of the invention, then placed in the beaker respectively added 1.0 mL water, stirred for 1 to 2 minutes under the condition of 25° C. water bath, observed and if not totally dissolved, added water (not more than 200 mL in total) until it's completely dissolved. The test results are shown in the table below.

| Sample | Test results |
|---|---|
| ACP-196 | Less than 0.1 mg/mL |
| ACP-196 malate Form 1 | 1.43 mg/mL |
| ACP-196 hemifumarate Form 1 | 0.91 mg/mL |
| ACP-196 maleate Form 1 | 1.33 mg/mL |
| ACP-196 phosphate Form 1 | 4.0 mg/mL |
| ACP-196 sulfate Form 1 | 1.5 mg/mL |

The results showed that the solubility of ACP-196 malate Form 1, ACP-196 hemifumarate Form 1, ACP-196 maleate Form 1, ACP-196 phosphate Form 1 and ACP-196 sulfate Form 1 of the present invention in water are higher than that of ACP-196 of Preparation Example 1.

What is claimed is:

1. ACP-196 malate Form 1 having the structure shown in the formula (I) below,

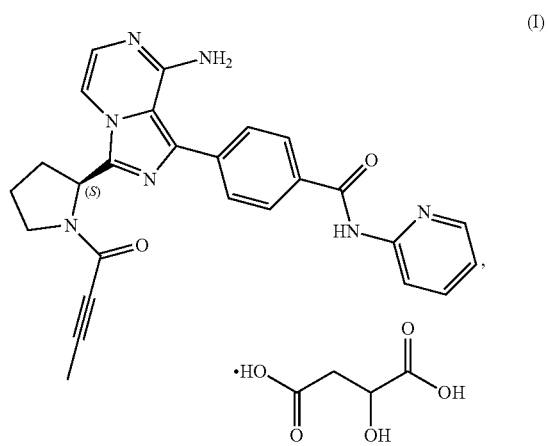

wherein, measured using Cu-Kα radiation, the X-ray powder diffraction pattern of the ACP-196 malate Form 1, expressed as 2θ angles, has the following characteristic peaks: 6.2°±0.2°, 8.9°±0.2°, 12.0°±0.2°, 12.4°±0.2°, 16.9°±0.2° and 22.9°±0.2°.

2. The ACP-196 malate Form 1 according to claim 1, wherein the X-ray powder diffraction pattern of the ACP-196 malate Form 1, expressed as 2θ angles, has the following characteristic peaks: 6.2°±0.2°, 8.9°±0.2°, 12.0°±0.2°, 12.4°±0.2°, 15.6°±0.2°, 16.9°±0.2°, 19.6°±0.2° 20.3°±0.2°, 20.7°±0.2°, 22.9°±0.2°, 23.8°±0.2° and 27.6°±0.2°.

3. The ACP-196 malate Form 1 according to claim 2, wherein the X-ray powder diffraction pattern of the ACP-196 malate Form 1, expressed as 2θ angles, has the following characteristic peaks and relative intensity:

| Diffraction angel 2θ | Relative intensity % |
|---|---|
| 6.2° ± 0.2° | 81.9 |
| 8.9° ± 0.2° | 21.3 |
| 12.0° ± 0.2° | 70.1 |
| 12.4° ± 0.2° | 100.0 |
| 12.9° ± 0.2° | 8.7 |
| 15.6° ± 0.2° | 12.5 |
| 16.9° ± 0.2° | 22.5 |
| 17.9° ± 0.2° | 10.9 |
| 18.7° ± 0.2° | 7.7 |
| 19.6° ± 0.2° | 21.5 |
| 20.3° ± 0.2° | 16.3 |
| 20.7° ± 0.2° | 16.9 |
| 21.2° ± 0.2° | 10.7 |
| 22.9° ± 0.2° | 32.7 |
| 23.8° ± 0.2° | 28.8 |
| 24.9° ± 0.2° | 12.1 |
| 26.3° ± 0.2° | 9.7 |
| 27.6° ± 0.2° | 17.6. |

4. A method of preparing the ACP-196 malate Form 1 according to claim 1, comprising any one of the following methods:
   1) dissolving ACP-196 and malic acid respectively in a solvent to form solutions, then mixing and stirring for crystallization and precipitation, and then separating and drying to obtain the ACP-196 malate Form 1; wherein:
the solvent is an alcohol or a ketone;
the weight to volume ratio of ACP-196 to the solvent when the solution is formed is from 30 mg/mL to 100 mg/mL;
the molar ratio of ACP-196 to malic acid is from 1:0.8 to 1:1.1;
the stirring time is 1 day to 2 days; and
the operation is carried out at room temperature; or
2) forming a solution of a mixture of ACP-196 and malic acid in a co-solvent, adding anti-solvent, stirring for crystallization and precipitation, and then separating and drying to obtain the ACP-196 malate Form 1; wherein:
the co-solvent is selected from the group consisting of ethyl acetate, isopropyl acetate, tetrahydrofuran, 1,4-dioxane, acetonitrile, dichloromethane, and chloroform;
the weight to volume ratio of ACP-196 to the co-solvent is from 20 mg/mL to 100 mg/mL;
the molar ratio of ACP-196 to malic acid is from 1:0.8 to 1:1.1;
the anti-solvent is selected from the group consisting of an ether, an alkane, and toluene;
the stirring time is from 1 day to 3 days; and
the operation is carried out at room temperature.

5. The method according to claim 4, wherein the solvent is isopropanol and wherein the weight to volume ratio of ACP-196 to the solvent is from 30 mg/mL to 50 mg/mL.

6. The method according to claim 4, wherein the co-solvent is tetrahydrofuran and wherein the weight to volume ratio of ACP-196 to the co-solvent is from 20 mg/mL to 50 mg/mL.

7. The method according to claim 4, wherein the anti-solvent is isopropyl ether.

8. The method according to claim 4, wherein ACP-196 and malic acid use the same solvent to form a solution.

9. A pharmaceutical composition comprising a therapeutically effective amount of the ACP-196 malate Form 1 according to claim 1, and at least one pharmaceutically acceptable carrier or additive.

10. A method of preparing the ACP-196 sulfate Form 1 having the structure shown in the formula (V) below,

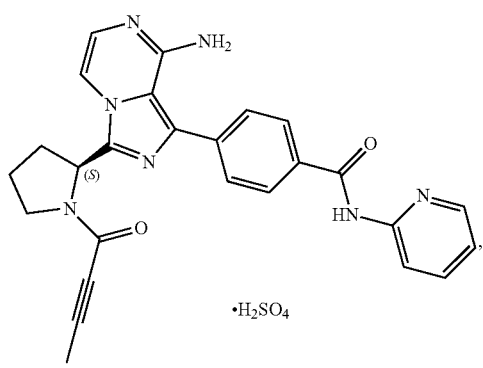

·H$_2$SO$_4$ (V)

wherein, measured using Cu-Kα radiation, the X-ray powder diffraction pattern of the ACP-196 sulfate Form 1, expressed as 2θ angles, has the following characteristic peaks: 8.9°±0.2°, 9.7°±0.2°, 17.5°±0.2°, 19.6°±0.2°, 21.9°±0.2°, and 23.6°±0.2°, the method comprising any one of the following methods:
1) dissolving ACP-196 and sulfuric acid respectively in a solvent to form solutions, then mixing and stirring for crystallization and precipitation, and then separating and drying to obtain the ACP-196 sulfate Form 1; wherein:
the solvent is an alcohol or a ketone;
the weight to volume ratio of ACP-196 to the solvent when the solution is formed is from 30 mg/mL to 100 mg/mL;
the molar ratio of ACP-196 to sulfuric acid is from 1:0.8 to 1:1.1;
the stirring time is 1 day to 2 days; and
the operation is carried out at room temperature; or
2) forming a solution of ACP-196 in a co-solvent, dropwisely adding sulfuric acid and anti-solvent, stirring for crystallization and precipitation, and then separating and drying to obtain the ACP-196 sulfate Form 1; wherein:
the co-solvent is selected from the group consisting of ethyl acetate, isopropyl acetate, tetrahydrofuran, 1,4-dioxane, acetonitrile, dichloromethane, and chloroform;
the weight to volume ratio of ACP-196 to the co-solvent is from 10 mg/mL to 500 mg/mL;
the molar ratio of ACP-196 to sulfuric acid is from 1:0.8 to 1:1.1;
the anti-solvent is selected from the group consisting of an ether, an alkane, and toluene;
the stirring time is from 1 day to 3 days; and
the operation is carried out at room temperature,
wherein the solvent is isopropanol and wherein the weight to volume ratio of ACP-196 to the solvent is from 30 mg/mL to 50 mg/mL.

11. The method according to claim 10, wherein the co-solvent is ethyl acetate and wherein the weight to volume ratio of ACP-196 to the co-solvent is from 25 mg/mL to 50 mg/mL.

12. The method according to claim 10, wherein the anti-solvent is n-hexane.

13. The method according to claim 10, wherein the X-ray powder diffraction pattern of the ACP-196 sulfate Form 1, expressed as 2θ angles, has the following characteristic peaks: 4.6°±0.2°, 7.9°±0.2°, 8.9°±0.2°, 9.7°±0.2°, 14.6°±0.2°, 15.0°±0.2°, 17.5°±0.2°, 19.6°±0.2°, 20.0°±0.2°, 21.9°±0.2°, 23.6°±0.2° and 25.9°±0.2°.

14. The method according to claim 13, wherein the X-ray powder diffraction pattern of the ACP-196 sulfate Form 1, expressed as 2θ angles, has the following characteristic peaks and relative intensity:

| Diffraction angel 2θ | Relative intensity % |
|---|---|
| 4.6° ± 0.2° | 21.6 |
| 7.9° ± 0.2° | 14.2 |
| 8.9° ± 0.2° | 41.9 |
| 9.7° ± 0.2° | 70.4 |
| 14.6° ± 0.2° | 21.2 |
| 15.0° ± 0.2° | 20.7 |
| 17.5° ± 0.2° | 100.0 |
| 17.8° ± 0.2° | 47.5 |
| 19.6° ± 0.2° | 50.7 |
| 20.0° ± 0.2° | 31.4 |
| 21.9° ± 0.2° | 59.7 |
| 23.6° ± 0.2° | 53.3 |
| 24.3° ± 0.2° | 31.8 |

-continued

| Diffraction angel 2θ | Relative intensity % |
|---|---|
| 24.8° ± 0.2° | 18.5 |
| 25.6° ± 0.2° | 27.9 |
| 25.9° ± 0.2° | 33.4 |
| 27.1° ± 0.2° | 16.0 |
| 27.5° ± 0.2° | 13.2 |
| 28.0° ± 0.2° | 8.2 |
| 29.2° ± 0.2° | 26.7 |
| 30.2° ± 0.2° | 11.1 |
| 31.6° ± 0.2° | 13.3. |

* * * * *